(12) United States Patent
Gauthier et al.

(10) Patent No.: US 10,046,445 B2
(45) Date of Patent: Aug. 14, 2018

(54) ELECTRONIC TORQUE WRENCH

(71) Applicant: Gauthier Biomedial, Inc., Grafton, WI (US)

(72) Inventors: Michael T. Gauthier, Grafton, WI (US); Austin R. Braganza, Milwaukee, WI (US); Dean C. Jeutter, Grafton, WI (US); Stacy Ann Gauthier, Grafton, WI (US)

(73) Assignee: Gauthier Biomedical, Inc., Grafton, WI (US)

( * ) Notice: Subject to any disclaimer, the term of this patent is extended or adjusted under 35 U.S.C. 154(b) by 282 days.

(21) Appl. No.: 15/153,024

(22) Filed: May 12, 2016

(65) Prior Publication Data

US 2016/0256989 A1 Sep. 8, 2016

Related U.S. Application Data

(63) Continuation of application No. 14/091,023, filed on Nov. 26, 2013, now Pat. No. 9,358,672, which is a (Continued)

(51) Int. Cl.
*B25B 23/142* (2006.01)
*A61B 17/88* (2006.01)
(Continued)

(52) U.S. Cl.
CPC ...... *B25B 23/1425* (2013.01); *A61B 17/8875* (2013.01); *B25B 15/04* (2013.01);
(Continued)

(58) Field of Classification Search
CPC ... B25B 23/1425; B25B 23/147; B25B 15/00; B25B 15/02; B25B 15/04; B25B 21/00;
(Continued)

(56) References Cited

U.S. PATENT DOCUMENTS 4,234,158 A 11/1980 Rollins et al.
5,207,697 A 5/1993 Carusillo et al.
(Continued)

FOREIGN PATENT DOCUMENTS

DE 202007012866 1/2008

*Primary Examiner* — David B Thomas
(74) *Attorney, Agent, or Firm* — Boyle Fredrickson, S.C.

(57) ABSTRACT

A torque wrench for use in driving fasteners is provided. The wrench includes an electronics unit disposed within a housing engaged with the body of the wrench that is capable of sensing and measuring the torque applied to a fastener by the wrench and providing an output of the level of torque to the user. The data sensed by the electronics unit can be utilized to provide feedback to the user regarding the operation of the wrench, and to monitor the overall operation of the wrench for calibration purposes, among other functions. During use, the wrench can provide the user with visual, audible and tactile feedback regarding the operation of the device relative to stored maximum torque values stored in the electronics unit. The housing for the electronics unit can be formed to be a single use component of the tool or can be designed for multiple uses with a configuration that can be engaged with cradles forming the body of the wrench having various different configurations.

11 Claims, 42 Drawing Sheets

Related U.S. Application Data continuation-in-part of application No. 13/915,395, filed on Jun. 11, 2013, now Pat. No. 8,714,058, which is a continuation of application No. 13/110,446, filed on May 18, 2011, now Pat. No. 8,485,075.

(60) Provisional application No. 61/784,396, filed on Mar. 14, 2013, provisional application No. 61/729,918, filed on Nov. 26, 2012, provisional application No. 61/345,817, filed on May 18, 2010.

(51) Int. Cl.
- *B25B 21/00* (2006.01)
- *B25B 15/04* (2006.01)
- *B25G 1/00* (2006.01)
- *B25H 3/00* (2006.01)
- *A61B 90/00* (2016.01)

(52) U.S. Cl.
CPC ............ *B25B 21/004* (2013.01); *B25G 1/005* (2013.01); *B25H 3/006* (2013.01); *A61B 2090/066* (2016.02); *A61B 2090/0813* (2016.02)

(58) Field of Classification Search
CPC . B25B 21/002; B25B 21/004; A61B 17/8875; A61B 2090/065; A61B 2090/0813; B25G 1/00; B25G 1/002; B25G 1/005; B25H 3/006
See application file for complete search history.

(56) References Cited

U.S. PATENT DOCUMENTS

| | | | |
|---|---|---|---|
| 5,476,014 A | 12/1995 | Lampe et al. | |
| 5,613,585 A | 3/1997 | Tiede | |
| 6,070,506 A | 6/2000 | Becker | |
| 6,109,150 A | 8/2000 | Saccomanno, III | |
| 6,138,539 A | 10/2000 | Carchidi et al. | |
| 6,439,086 B1 | 8/2002 | Bahr | |
| 6,487,943 B1 | 12/2002 | Jansson et al. | |
| 6,516,185 B1 | 2/2003 | MacNally | |
| 6,807,885 B2 | 10/2004 | Loper | |
| 6,981,436 B2 | 1/2006 | Becker et al. | |
| 6,995,549 B2 | 2/2006 | Walters | |
| 7,021,180 B2 | 4/2006 | Crane | |
| 7,107,884 B2 | 9/2006 | Cutler et al. | |
| 7,172,561 B2 | 2/2007 | Grinberg | |
| 7,236,056 B2 | 6/2007 | Chang | |
| 7,272,999 B2 | 9/2007 | Cutler et al. | |
| 7,334,509 B1 | 2/2008 | Gao | |
| 7,367,250 B2 | 5/2008 | Rainone et al. | |
| 7,430,945 B2 | 10/2008 | Gauthier et al. | |
| 7,469,619 B2 | 12/2008 | Anjanappa et al. | |
| 7,650,821 B2 | 1/2010 | Gauthier et al. | |
| 7,740,628 B2 | 6/2010 | Hoegerle et al. | |
| 7,762,164 B2 | 7/2010 | Nino et al. | |
| 7,823,485 B2 | 11/2010 | Rainone | |
| 7,863,876 B2 | 1/2011 | Cook et al. | |
| 7,913,594 B2 | 3/2011 | Gauthier et al. | |
| 7,938,046 B2 | 4/2011 | Nino et al. | |
| 8,037,790 B2 | 10/2011 | Gauthier | |
| 8,051,720 B2 | 11/2011 | Schwyn et al. | |
| 8,485,075 B1 | 7/2013 | Gauthier et al. | |
| 8,529,567 B2 * | 9/2013 | Garcia | A61B 17/162 606/104 |
| 8,714,058 B2 | 5/2014 | Gauthier et al. | |
| 8,786,233 B2 | 7/2014 | Fair et al. | |
| 9,358,672 B2 * | 6/2016 | Gauthier | A61B 17/8875 |
| 9,505,109 B2 * | 11/2016 | Gauthier | B25B 23/1425 |
| 2003/0114860 A1 | 6/2003 | Cavagna et al. | |
| 2004/0134316 A1 | 7/2004 | Loper | |
| 2005/0268750 A1 | 12/2005 | Bruce et al. | |
| 2006/0089622 A1 | 4/2006 | Bourne et al. | |
| 2006/0156874 A1 | 7/2006 | Hsieh | |
| 2006/0179981 A1 | 8/2006 | Cutler et al. | |
| 2008/0006130 A1 | 1/2008 | Hsieh | |
| 2008/0016990 A1 | 1/2008 | Rinner | |
| 2009/0178519 A1 | 7/2009 | Hsieh | |
| 2009/0249924 A1 | 10/2009 | Lin | |
| 2010/0000381 A1 | 1/2010 | Takahashi | |
| 2010/0170370 A1 | 7/2010 | Yokoyama et al. | |
| 2010/0206141 A1 | 8/2010 | Nakata et al. | |
| 2011/0064978 A1 | 3/2011 | McGahan | |
| 2011/0152867 A1 | 6/2011 | Petrzelka et al. | |
| 2011/0314973 A1 | 12/2011 | Tsai | |
| 2012/0042754 A1 | 2/2012 | Chen | |
| 2013/0291694 A1 | 11/2013 | Gauthier et al. | |

* cited by examiner

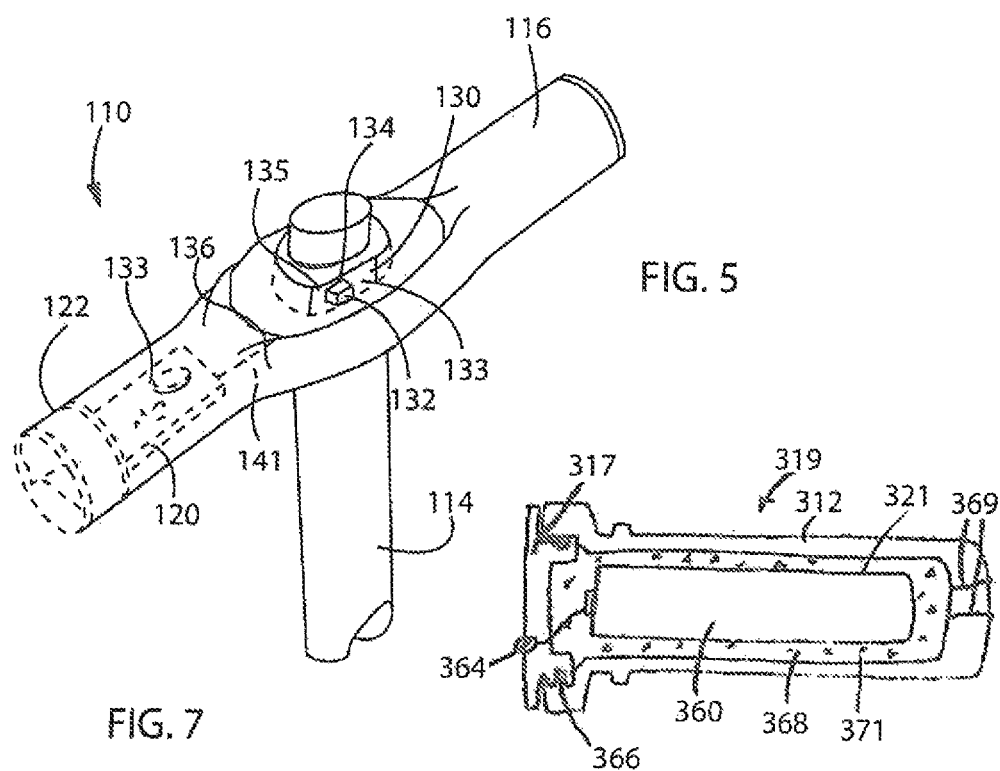
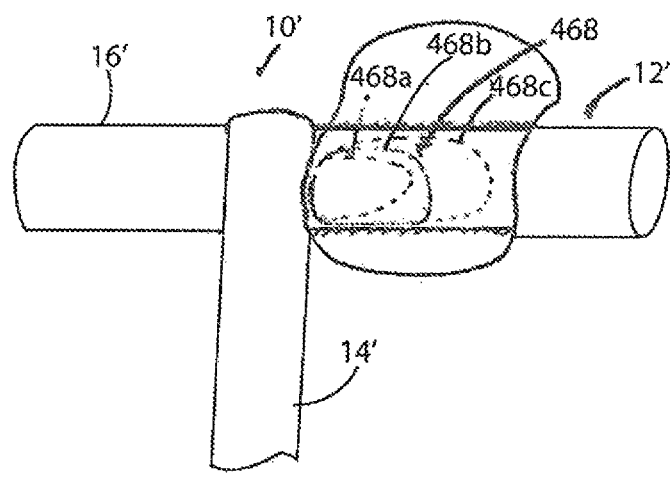

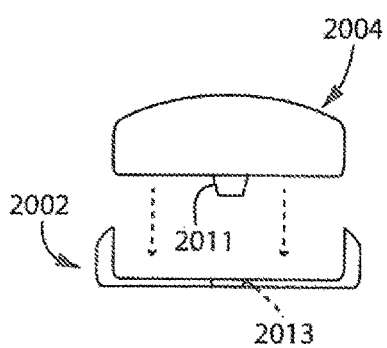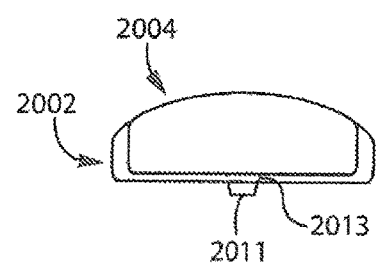
FIG. 28A          FIG. 28B
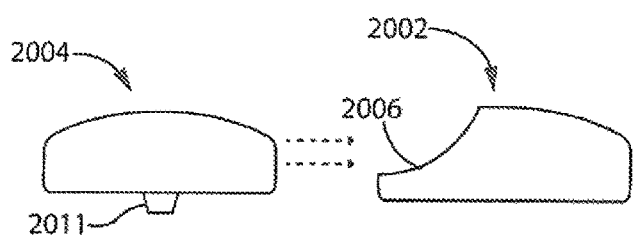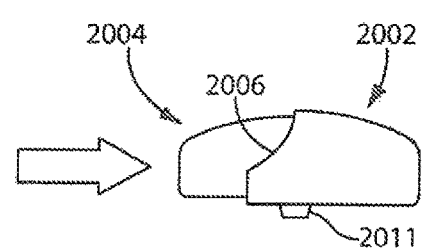
FIG. 29A          FIG. 29B

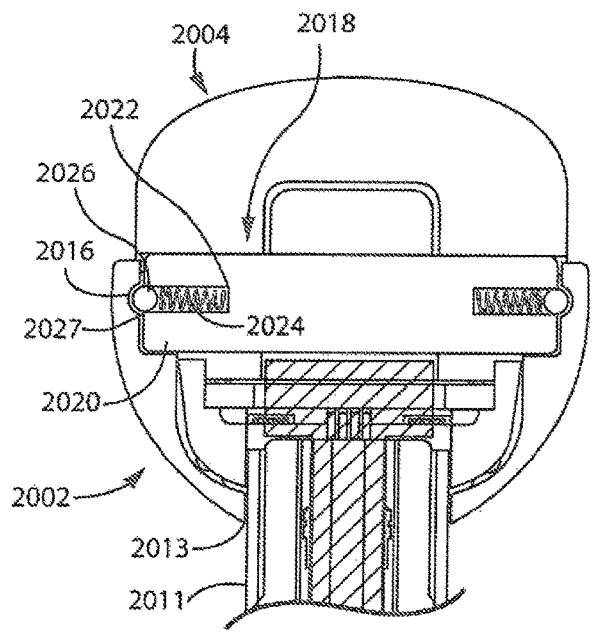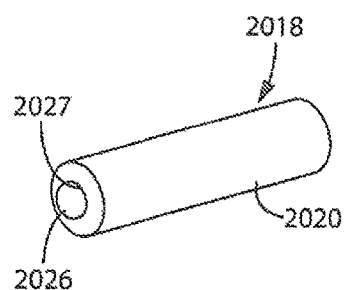
FIG. 31    FIG. 32
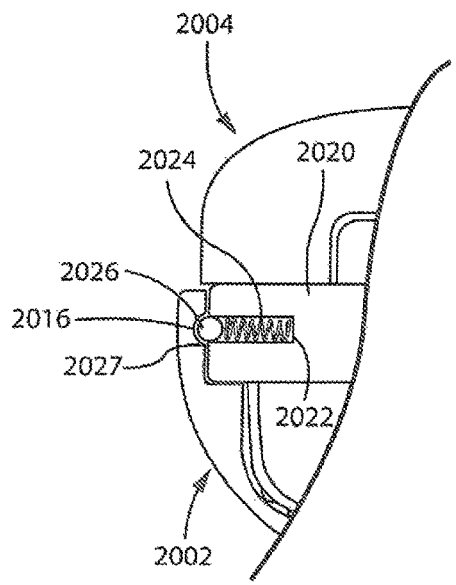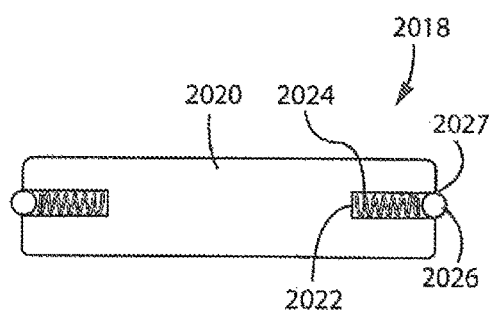
FIG. 33
FIG. 34

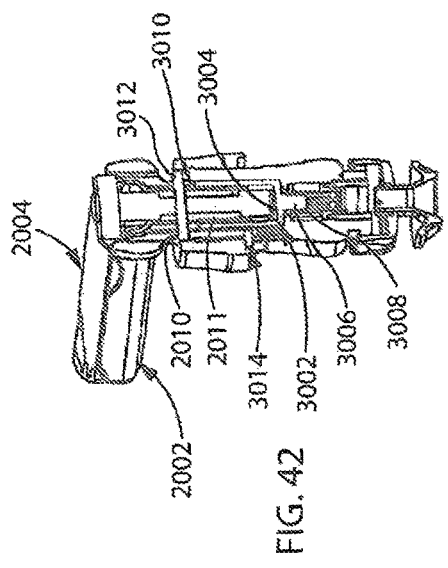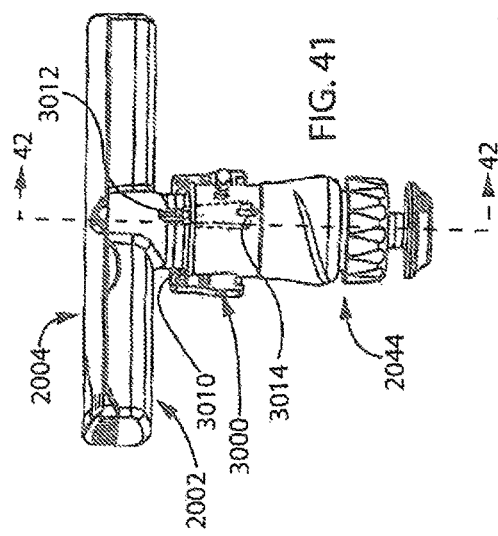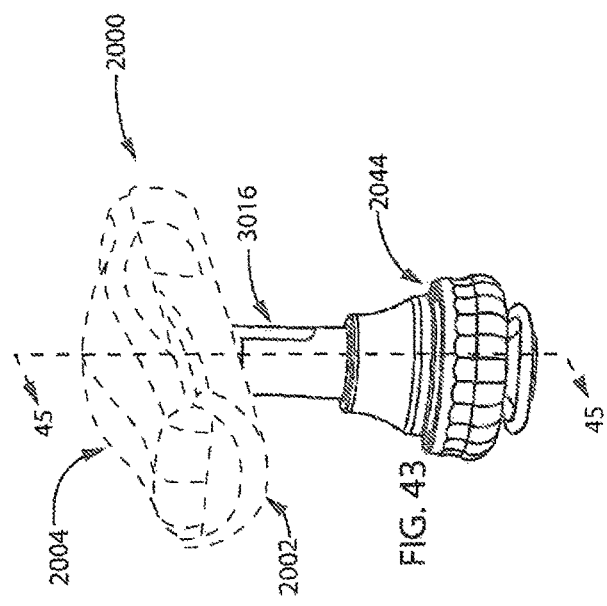

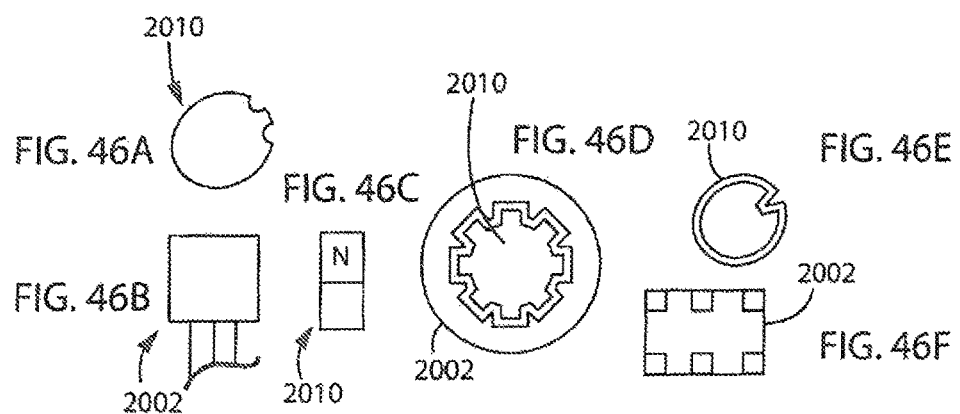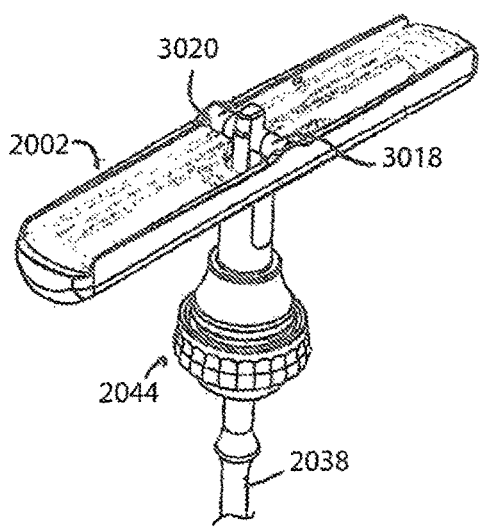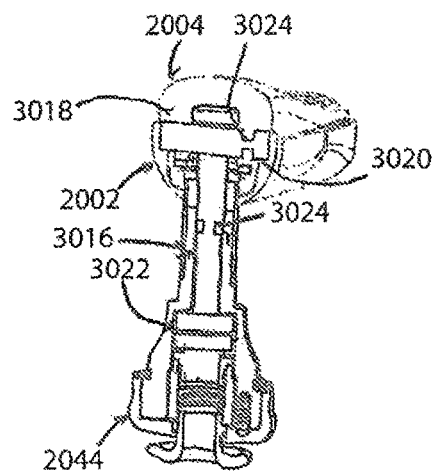

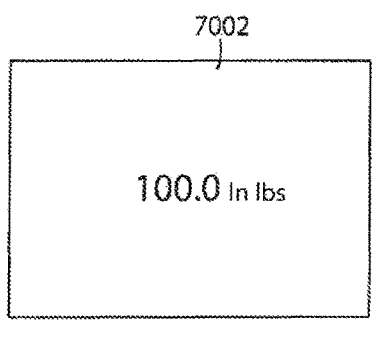
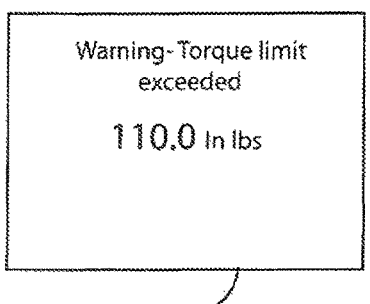
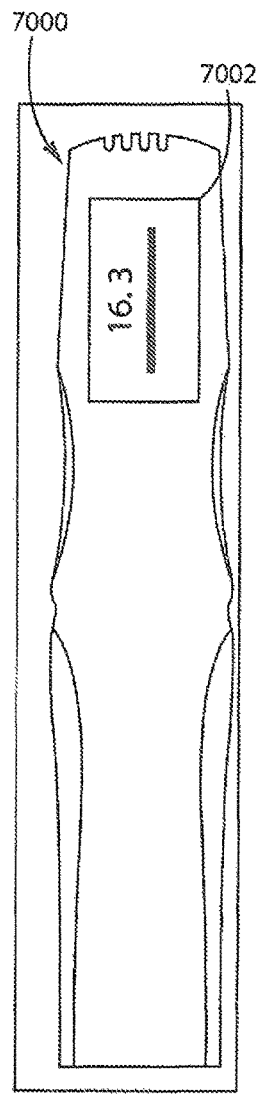
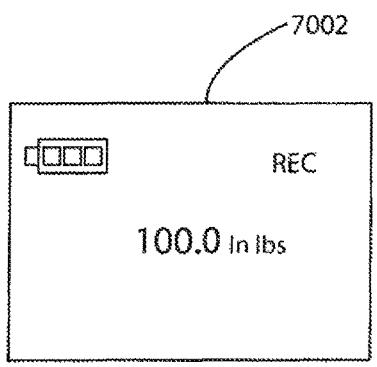
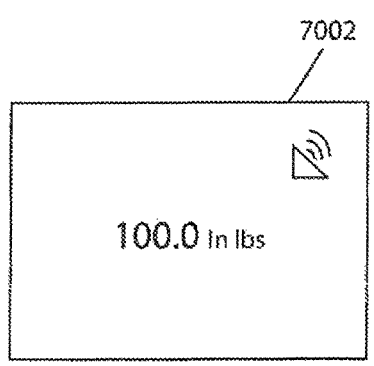
1. Torque in numbers with units
FIG. 59B
1a. Screen shows "Torque Limit exceeded" warning message
FIG. 59C
2. With record function and battery level indicator
FIG. 59D
3. With transmitting icon
FIG. 59E
Intellitorq with LCD display screen - concept
FIG. 59A

ELECTRONIC TORQUE WRENCH

CROSS-REFERENCE TO RELATED APPLICATIONS

This application is a continuation of U.S. Non-Provisional patent application Ser. No. 14/091,023, filed on Nov. 26, 2013, which is a continuation-in part of U.S. Non-Provisional patent application Ser. No. 13/915,395, filed on Jun. 11, 2013, now U.S. Pat. No. 8,714,058, which is a continuation of U.S. Non-Provisional patent application Ser. No. 13/110,446, filed on May 18, 2011, now U.S. Pat. No. 8,485,075, which in turn claims priority from U.S. Provisional Application Ser. No. 61/345,817, filed on May 18, 2010, and this application also claims priority from U.S. Provisional Patent Application Ser. No. 61/729,918 filed on Nov. 26, 2012, and U.S. Provisional Patent Application Ser. No. 61/784,396, filed on Mar. 14, 2013, the entirety of which are each expressly incorporated by reference herein.

FIELD OF THE INVENTION

The present invention relates to tools, and more specifically to tools including electronic measuring and display device for providing indication of the forces being applied by the tools.

BACKGROUND OF THE INVENTION

Often, fasteners used to assemble performance critical components are tightened to a specified torque level to introduce a "pretension" in the fastener. As torque is applied to the head of the fastener, beyond a certain level of torque the fastener begins to stretch. This stretch results in the pretension in the fastener which then holds the components together. A popular method of tightening these fasteners is to use a torque wrench. Accurate and reliable torque wrenches help insure the fasteners are tightened to the proper torque specifications.

Torque wrenches vary from simple mechanical types to sophisticated electronic types. Mechanical type torque wrenches are generally less expensive than electronic ones. There are two common types of mechanical torque wrenches, beam and clicker types. With a beam type torque wrench, a beam bends relative to a non-deflecting beam in response to the torque being applied with the wrench. The amount of deflection of the bending beam relative to the non-deflecting beam indicates the amount of torque applied to the fastener. Clicker type torque wrenches work by preloading a snap mechanism with a spring to release at a specified torque, thereby generating a click noise. Other types of mechanical torque wrenches include indicating, ratcheting, torque limiting, in-line and beam styles of torque wrenches. In an indicating wrench, torque value is measured and displayed on a scale. In a torque limiting wrench, the wrench will drive the fastener until a preset torque value is reached at which point the wrench will slip and cease to transmit the torque applied. In a ratcheting mechanism wrench, in order to drive a fastener into a substrate such as wood or bone it is necessary to rotate the fastener through multiple rotations about its axis. For a hand held tool, in order to drive fasteners, typically the user will have to change their grip or change hands in order to keep driving the fastener due to the limitation of the range of motion of the bones joint in a human hand, which occurs at approximately 100 to 180 degrees depending on the person. A ratcheting mechanism in a fastener driver tool allows the user to rotate the instrument in the opposite direction to the torque being applied without lifting or otherwise disengaging the device driving bit from the fastener and without lifting the hand off the device or changing hands. With a ratcheting mechanism in the tool the user can rotate the tool and drive the fastener through as many degrees of rotation as their hand allows and then ratchet the driving tool in the opposite direction so as to be able to drive the fastener through as many degrees without lifting the hand off the driving tool.

Electronic torque wrenches (ETWs) tend to be more expensive than mechanical torque wrenches, and more accurate as well. When applying torque to a fastener with an electronic torque wrench, the torque readings indicated on the display device of the electronic torque wrench in a visible manner, such as by a numeric or light indication, and are proportional to the pretension in the fastener due to the applied torque. However, the readings also depend on, among other factors, the under head friction between the head of the fastener and the adjacent surface of the component and the friction between the mating threads. Static friction is greater than dynamic friction. Therefore, when torquing operations are initiated, increased amounts of torque may be required to overcome static friction forces and initiate rotation of the fastener. Therefore, it follows that torque is preferably applied to the fastener in a slow and continuous manner to allow friction forces to stabilize, to help insure accuracy and to help prevent over-torquing, which can result in damage being done to the fastener or the substrate, with extreme cases resulting in destruction of the fastener or substrate. As well, it is often desirable for the user to see both the current torque value (torque being applied at that instant) and the peak torque value (maximum torque applied up to the present instant) simultaneously. However, existing torque wrenches typically display only the current torque value or the peak torque value at any given time.

When a torque wrench is operated in a "tracking mode," the current torque value is displayed and the user therefore does not necessarily get immediate feedback regarding the actual peak torque value to which the fastener may have been subjected. Although with some electronic torque wrenches it is possible to get this information by downloading the data, this action is typically not instantaneous and, therefore, the operator does not get immediate feedback. On the other hand, when operating in a "peak hold mode," the display of the electronic torque wrench typically shows only the maximum torque applied to the fastener up to that time. In the peak hold mode, the user is often ignorant of the current torque level, which can lead to either over or under-torquing the fastener.

Another factor that can affect the accuracy of a reading on an electronic torque wrench is the operating temperature. Strain gages that are used in electronic torque wrenches to measure applied torque are often affected by temperature. Therefore, to obtain accurate torque measurements, it is often necessary to measure the existing temperature and adjust the displayed torque value for a given strain gauge reading.

Regardless of which type ETW is used, torque extensions may be required to tighten fasteners that are in locations that the torque wrench will not reach. One of the most common methods of attaching a torque extension to an ETW is to replace the original drive head with an extension that has its own drive head. Once the extension is inserted, the readings of the ETW must usually be corrected for any change in lever arm length due to the extension. With the extension in place, the actual torque experienced by the fastener will be either higher or lower than what is actually displayed on the ETW, depending on whether the extension extends outwardly or inwardly from the end of the ETW, respectively.

For each different length extension, a different correction factor must be calculated. Typically, the end user calculates a correction factor and either divides or multiplies the desired final actual torque value to be applied to the fastener by this correction factor to determine the final compensated set torque value (as displayed by the ETW) that is to be input into the ETW. Whether the actual torque value is divided by or multiplied by the correction factor is dependent upon the method of determining the correction factor. The final compensated set torque value is the value at which, when displayed, the user ceases to apply torque to the fastener. Typically, the user will only know the final compensated set torque value accurately and is not able to accurately determine the intermediate torque values. In other words, the user only calculates the final compensated set torque value for the set torque and will not be able to continuously monitor the actual torque values during torquing operations as only "compensated" values are displayed by the ETW. This situation can lead to over and under-torquing, possibly resulting in loss of performance of the fasteners.

Further, with regard to prior art electronic torque wrenches, the applications of each of these types of wrenches are normally within environments where the cleanliness of the wrench is not an issue, such as in automotive repair shops. As such, the ability of the prior art electronic torque wrench to be cleaned to a sterile level is not a requirement for the construction of the electronic torque wrench, and correspondingly the design and construction of these prior art wrenches is not capable of protecting the internal electronic components of these types of wrenches to enable the electronic torque wrenches to be utilized in environments where the wrench is required to be sterilized prior to use.

Thus, it is desirable to develop an electronic torque wrench that is capable of withstanding the temperatures and pressures required to sterilize the device in order to protect the internal components of the device. Alternatively, it is desirable to develop an electronic torque wrench capable of being operated in a sterile environment that can be sterilized and that includes one or more disposable components that are operably connectable to the wrench for operation of the wrench but that do not require sterilization after their initial use.

SUMMARY OF THE INVENTION

According to one aspect of the present invention, an electronic torque wrench is provided for engaging a workpiece in a sterile environment, the electronic torque wrench including a wrench body with a wrench head disposed on the wrench body, wherein the wrench head is configured to engage the workpiece. A grip handle is disposed on the wrench body opposite the wrench head and a user interface is carried by the wrench body which is also connected to a microprocessor disposed within the handle, or optionally at a location spaced from the handle. In one embodiment, the user interface includes a display with a first readout and a second readout, and an input device for inputting a preset torque value, all of which are operably connected to the microprocessor. The first readout displays a peak torque value continuously during operations and the second readout displays an applied torque value continuously during operations.

According to another aspect of the present invention, a method is provided of displaying a peak torque value and an applied torque value as a percentage of a preset torque value on a display of an electronic torque wrench during a torquing operation on a workpiece in a sterile environment. The method includes one or more of the steps of: inputting the preset torque value into the electronic torque wrench, the preset torque value being the maximum torque that is desired to be applied to the workpiece; detecting a current torque being applied to the workpiece; comparing the current torque to an existing peak torque value displayed on the display; displaying the current torque on the digital display as the peak torque value when the current torque exceeds the displayed peak torque value; comparing the current torque to the preset torque value to determine a percentage of the preset torque value that the current torque corresponds to; and displaying the percentage on the display such that the percentage and the peak torque value are displayed simultaneously at all times during the torquing operation.

According to still another aspect of the present invention, an electronic torque wrench for driving a workpiece in a sterile environment is provided in which the torque wrench includes a wrench body having a handle end and a wrench head receiving end. A wrench head includes a workpiece receiving end and a mounting end that is removably received by the wrench head receiving end of the wrench body. A wrench head sensing device is carried by the wrench head receiving end and includes an electrical connection between the wrench head sensing device and the microprocessor so that the wrench head sensing device can send an electrical signal to the microprocessor indicating the presence of the wrench head on the wrench head receiving end.

According to still another aspect of the present invention, an electronic torque wrench is provided with torque adjustment capability, display of desired torque settings, actual torque achieved display, torque measuring capability and optionally a shutoff at a predetermined torque level. The electronic torque wrench provides repeatable and accurate torque application without regard to operator capability within a sterile operating environment.

Among the several features, objects and advantages of the present invention are the provision of an improved torque-applying wrench which:

measures applied torque precisely by electronically sensing torque during operation;

allows convenient operator selection of the predetermined torque level and displays the predetermined torque level;

does not require external sensing and control circuits but are instead integrated completely into the tool in a manner that enables the wrench to be utilized in a sterile environment;

provides for torque sensing and torque control by electronic feedback;

does not require an external source of electrical power but is instead capable of long-term use solely under battery power;

can be integrated into typical configurations of existing torque wrenches by use of sensing and control elements which will not interfere with normal speed and convenience of operation of the torque wrench;

uses a torque-sensing technology of such significant economy and relative simplicity as to make possible portable digital torque-responsive, and optionally torque-controlling wrenches; and provides such torque-responsive, and optionally torque-controlling tools with such economy and simplicity as to be suited for medical use in sterile environments, as well as use in many other technical areas.

The present disclosure relates to an electronic torque wrench apparatus, system associated with the apparatus, and method of using the apparatus and the system for use in attaching fasteners and other tool operations in a sterile medical environment. Securing the fastening components at a desired torque setting allows for secure attachment of the components and any structures related thereto without under-tightening or over-tightening the components. Under-tightening the components could result in disengagement of the components. Over-tightening the components could make disengaging the components difficult or could cause damage to the components. To prevent under-tightening or over-tightening a torque measurement can be made while tightening the components, to meet a target torque setting or to apply a torque within a desired torque range.

According to still a further aspect of the present invention, an electronic torque wrench apparatus, system, and method of using the apparatus and system is provided for tightening and standardizing the forces associated with a fastener system for medical procedures. In one embodiment, the system includes access to a database of fastener configuration information for various medical procedures, specifically as they relate to the particular individual on which the procedure is to be performed. Information is provided from the database to the wrench apparatus. The wrench apparatus provides verification of the information and verification of application of the information by the use of the wrench. After use, the wrench assembly transfers the information back to the system to provide a historical record of the procedure and the torque values applied by the physician using the wrench to the respective fasteners.

According to still another aspect of the present invention, the electronic torque wrench assembly includes a coupling device or coupler and the wrench. The coupling device receives information from the system and transfers it to the wrench. Once the fastener configuration information is received, the wrench is removed from the coupler and is used to establish torque settings for use in the fastener torque process. Verification of the tightening process is recorded at the wrench during use and transmitted back to the coupler. The coupler then transfers the information to the system.

According to still a further aspect of the present invention, the system includes a driving device management server which communicates with the microprocessor. The coupler is connected to the server to collect information about the procedure/subject from the server. The device management server then delivers corresponding fastener configuration information to the coupler for transfer to the electronic torque wrench. The wrench utilizes the information in the fastener tightening process to alert the physician of the proper torque value for the particular fastener being tightened in the procedure. Verification of the information can be recorded at and/or by the wrench and transferred back to the coupler when the wrench is placed in the coupler. Information transferred to the coupler can be transmitted to the procedure management server for verification, transaction completion and storage.

According to still another aspect of the present invention, the data regarding the use of the torque wrench in performing the fastener tightening procedure or process stored in the microprocessor can be transferred to the coupler and/or server to record the usage of the wrench. This data can be stored in the server for use in determining the necessary calibration for the wrench, based on various parameters such as the number of uses of the wrench, and the overall length of time of use of the wrench, among others.

According to still a further aspect of the present invention, the wrench can be configured to include a cradle. The cradle includes a slot, aperture or other suitable opening for the insertion of a power pack/sensor module that includes the electronic torque sensing device and is adapted to be engaged with the desired driving instrument or implement. The power pack/sensor module mates with the cradle to activate the power pack/sensor module, which is pre-calibrated and operable to provide feedback to the individual utilizing the tool regarding the level of torque being applied by the wrench.

According to still another aspect of the present invention, the power pack/sensor module can be designed to be pre-calibrated for accurate determination of the torque applied to a fastener in a single use, such that the power pack/sensor module can be disposed of after use in a single procedure or process.

According to another aspect of the present disclosure, the power pack/sensor module and cradle include lock out features that prevent operation of the power pack/sensor module when not properly interconnected. The power pack/sensor module can further be designed with a configuration that interconnected with different cradles having different implements or configurations, allowing a single power pack/sensor module to be engaged and/or utilized with multiple cradles.

According to still another aspect of the present invention, the cradle and/or the power pack/sensor module can be formed to be sterilizable, such that the cradle and/or the power pack/sensor module can be re-used in multiple procedures.

Other aspects, features and advantages of the present invention will be set forth in part in the description which follows and the accompanying drawings, wherein the embodiments of the disclosure are described and shown, and in part will become apparent upon examination of the following detailed description taken in conjunction with the accompanying drawings.

BRIEF DESCRIPTION OF THE DRAWINGS

The drawings illustrate the best mode currently contemplated of practicing the present invention.

In the drawings:

FIG. 5 is an isometric view of a third embodiment of an electronic driving tool constructed according to the present disclosure;

FIG. 7 is a cross-sectional view of power cell component of the tool of FIG. 1;

FIG. 8 is a cross-sectional view of a temperature compensation bladder or use with the tool of FIG. 1;

FIGS. 28A-28B are front plan views of a tenth embodiment of an electronic driving tool constructed according to the present disclosure;

FIGS. 29A-29B are front plan views of an eleventh embodiment of an electronic driving tool constructed according to the present disclosure;

FIG. 31 is a cross-sectional view of the tool of FIG. 30;

FIG. 32 is an isometric view of a locking member for a power source of the tool of FIG. 30;

FIG. 33 is a cross-sectional view of the locking member of FIG. 32:

FIG. 34 is a partially broken away, cross-sectional view of the tool of FIG. 30;

FIG. 41 is a partially broken away, isometric view of the tool of FIG. 40;

FIG. 42 is a cross-sectional view along line 42-42 of FIG. 41;

FIG. 43 is an isometric view of a seventeenth embodiment of an electronic driving too constructed according to the present invention;

FIG. 44 is a partially broken away, isometric view of the tool of FIG. 43;

FIG. 45 is a cross-sectional view along line 45-45 of FIG. 43;

FIGS. 46A-46F are views of alternative configurations for the electronic driving tool of FIG. 25;

DETAILED DESCRIPTION OF THE INVENTION

Reference will now be made in detail to various embodiments of the invention, one or more examples of which are illustrated in the accompanying drawings. Each example is provided by way of explanation, not limitation, of the invention. In fact, it will be apparent to those skilled in the art that modifications and variations can be made in the present invention without departing from the scope and spirit thereof. For instance, features illustrated or described as part of one embodiment may be used on another embodiment to yield a still further embodiment. Thus, it is intended that the present invention covers such modifications and variations as come within the scope of the appended claims and their equivalents.

Figure 1:
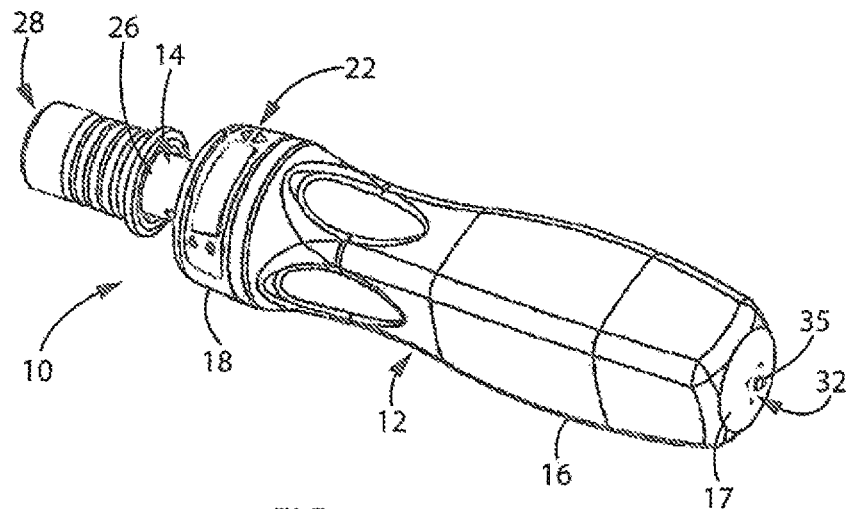
FIG. 1 is an isometric view of a first embodiment of an electronic driving tool constructed according to the present disclosure.
Figure 2:
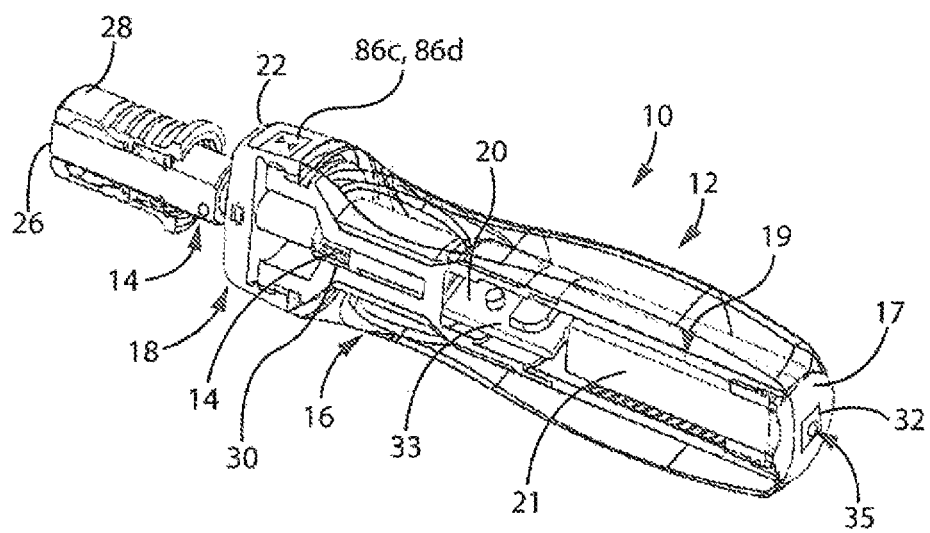
FIG. 2 is a cross-sectional view along line 2-2 of FIG. 1.

Referring now to FIGS. 1 and 2, an in-line electronic torque wrench 10 in accordance with the present invention is shown. The electronic torque wrench 10 includes a wrench body 12, a ratchet/wrench shaft 14, a resilient grip handle 16, a housing 18, a battery assembly 19, and an electronics unit 20 with a user interface or display 22. Preferably, wrench body 12 is of generally a tubular construction, and receives shaft 14 at a first end and a power supply or battery assembly 19 at a second end, secured therein by an end cap 17. Housing 18 is mounted therebetween and carries electronics unit 20.

As shown, a front end 26 of shaft 14 includes an adapter 28 connected to a suitable ratcheting mechanism (not shown) such as that shown in U.S. Pat. No. 7,413,065, incorporated by reference herein in its entirety. The adapter 28 is configured to receive variously sized sockets, extensions, etc. The adapter 28 can also be detachably connected to the shaft 14 by any suitable mechanism.

The attachment mechanism for securing the shaft 14 to the body 12 includes a sensor 30 configured to sense the torque or strain exerted by the wrench 10 through the shaft 14 onto a fastener (not shown). The sensor 30 can take any of a number of suitable forms, such as a strain gauge, a Hall sensor, and a piezoelectric sensor, among others.

The sensor 30 is operably connected to the electronics unit 20, such that the signal generated by the sensor 30 can be transmitted to the unit 20. Once in the unit 20, the unit 20 can utilize the signal for a variety of purposes, such as to calculate a torque value from the signal to provide a real-time indication of the torque applied via the wrench 10 on the display 22.

The operation of the electronics unit 20 and the sensor 30 is controlled by a switch 32 disposed on the body 12, and operably connected between the unit 20 and sensor 30, and the power supply 19 at the opposite end. Thus, the switch 32 enables power to be selectively applied to the unit 20 and sensor 30 as desired. The engagement of the housing 18, the body 12 the handle 16 and the end cap 17 provide an enclosure or barrier 33, which can also be formed separately, for the battery assembly 19, the electronics unit 20 and the sensor(s) 30 that enables the wrench 10 to be autoclaved for sterilization purposes without damaging the battery assembly 19, the electronics unit 20 or the sensor 30, as well as the display 22.

Figure 3:
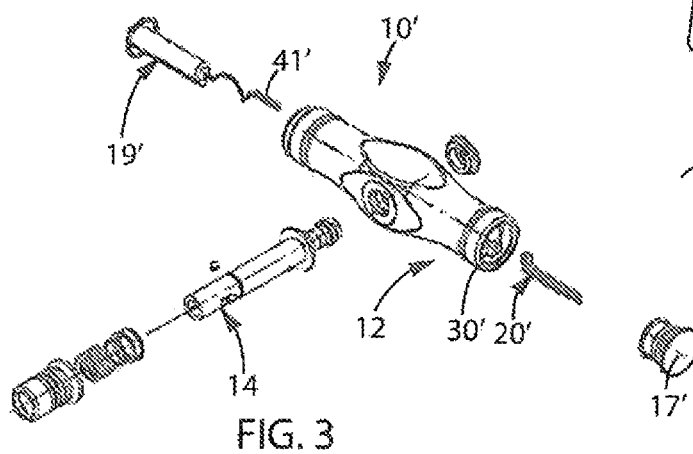
FIG. 3 is an exploded, isometric view of a second embodiment of an electronic driving tool constructed according to the present disclosure.
Figure 4:
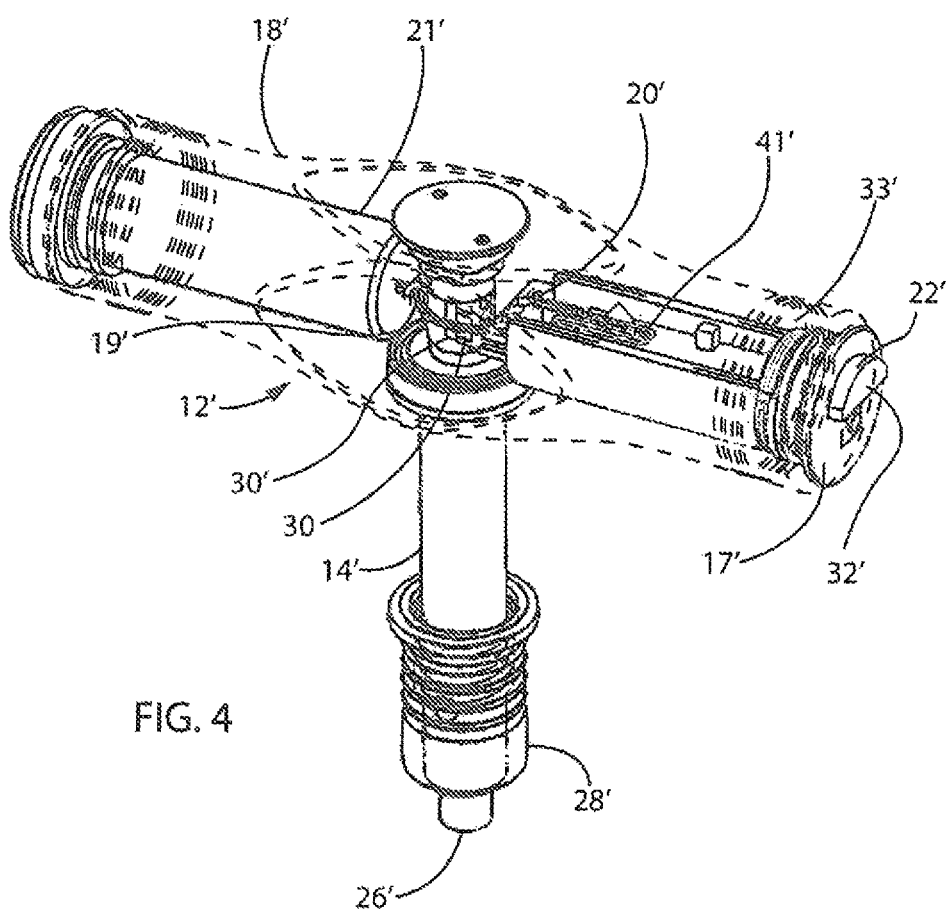
FIG. 4 is an isometric view of the interior components of the tool of FIG. 3.

Referring now to FIGS. 3 and 4, a second embodiment of the wrench 10' is illustrated. In this embodiment, the wrench 10' has a T-shape, with the shaft 14' extending perpendicularly from the body 12'. In the illustrated embodiment, the shaft 14' is disposed centrally on the body 12', such that the power source 19' and the electronics unit 20' are disposed on opposite sides of the body 12' within the body 12', such that the body 12' provides an enclosure for the power source 19' and the electronics unit 20' that enables the wrench 10' to be autoclaved for sterilization purposes without damaging the battery assembly 19' or the electronics unit 20'. Alternatively, the shaft 14' can be oriented to one side or the other of the body 12', as desired.

The shaft 14' can be connected directly to the body 12' or to a ratcheting mechanism (not shown) disposed within the body 12'. At the connection of the shaft 14' to the body 12', a sensor 30' is disposed to determine the strain or torque being applied by the wrench 10' through the shaft 14' to a fastener or other substrate (not shown) for representation on a suitable display (not shown) on the body 12'.

Referring now to FIG. 5, a third embodiment of the wrench 110 is illustrated. The wrench 110 has a T-shape similar to the embodiment of FIGS. 3 and 4, but includes a piezoelectric sensor 130 located within the body 112. The sensor 130 is formed of a first element 132 on a flat surface 133 of the shaft 114 and a second element 134 is disposed on an adjacent flat surface 135 of the body 112. The relative position of the elements 132 and 134 is determined by the electronics unit 120 disposed within the body 112, which is connected to the elements 132 and 134 by conductors 136 to receive signals from the elements 132 and 134.

Figure 6A:
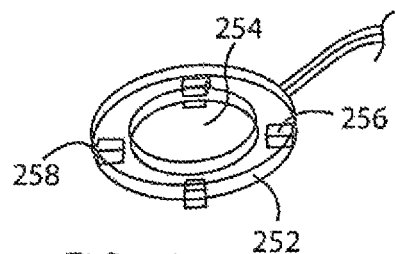
FIGS. 6 and 6A are isometric views of a lighting element utilized with the tool of FIG. 1.
Figure 6:
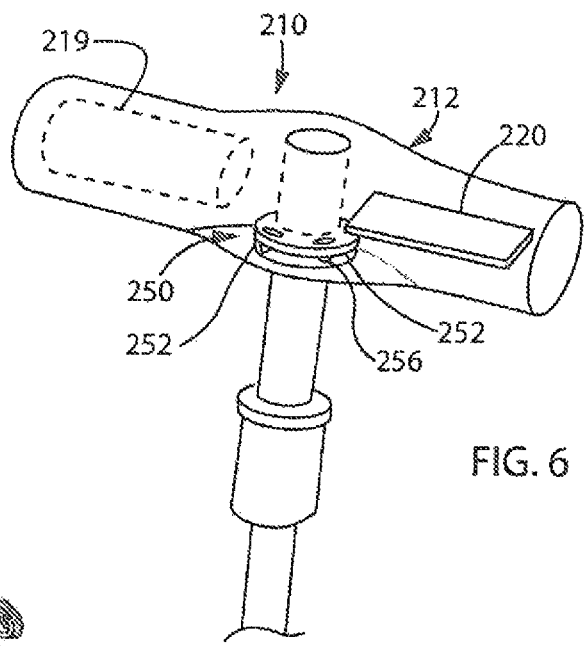

Looking now at FIGS. 6 and 6A, a driving tool or wrench 210 is shown in which the wrench 210 includes a light source 250. The light source 250 is formed with a generally circular housing 252 that has a central aperture 254 that is slightly larger in shape than the shaft 214, such that the housing 252 is positionable around the shaft 214 either immediately adjacent the body 212, or disposed within the body 212. In either configuration, the housing 252 includes a number of lighting elements 256 positioned thereon that are operably connected to the power source 219 and optionally to the electronic unit 220 which are positioned within the body 212, either directly or via an intervening member, such as the housing 252 if formed of a conductive material. The lighting elements 256 direct light downwardly from the body 212 along and around the shaft 214 to illuminate the area immediately surrounding the shaft 214, thereby providing a better viewing area for the individual operating the wrench 210.

Referring now to FIG. 7, a power source 319 of the wrench 10,10' is illustrated that includes a battery or power cell 360 positioned within a capsule 362 that is releasably engaged with a cap 364, such as via a threaded connection. The cap 364 is sealingly engaged with the capsule 362 by a sealing member 366 disposed between the capsule 362 and the cap 364. The power cell 360 is held within the capsule 366 by an insulating material 368 to prevent any inadvertent discharge of electricity from the power source 360 through the capsule 362. To facilitate the passage of power from the cell 360 to the wrench 10,10' when the capsule 362 is engaged with the body 12' of the wrench 10,10', conductors (not shown) are disposed within the capsule 362 and connect the power cell 360 with or through the cap 364 to the electronics unit 20,20' disposed within the body 12,12' of the wrench 10,10'.

In FIG. 8, the wrench 10' is shown as including an expandable bladder 468 within the body 12'. The bladder 468 can expand or contract within the body 12' as shown by the variations in size of the bladder shown by 468a, 468b and 468c in response to changes in the temperature or pressure of the environment in which the wrench 10' is located, such as when autoclaved, to further maintain the proper operation of the internal components of the wrench 10', e.g., the power source 19' and electronics unit 20', beyond the protection afforded by the body 12' or barrier 33.

Figure 9:
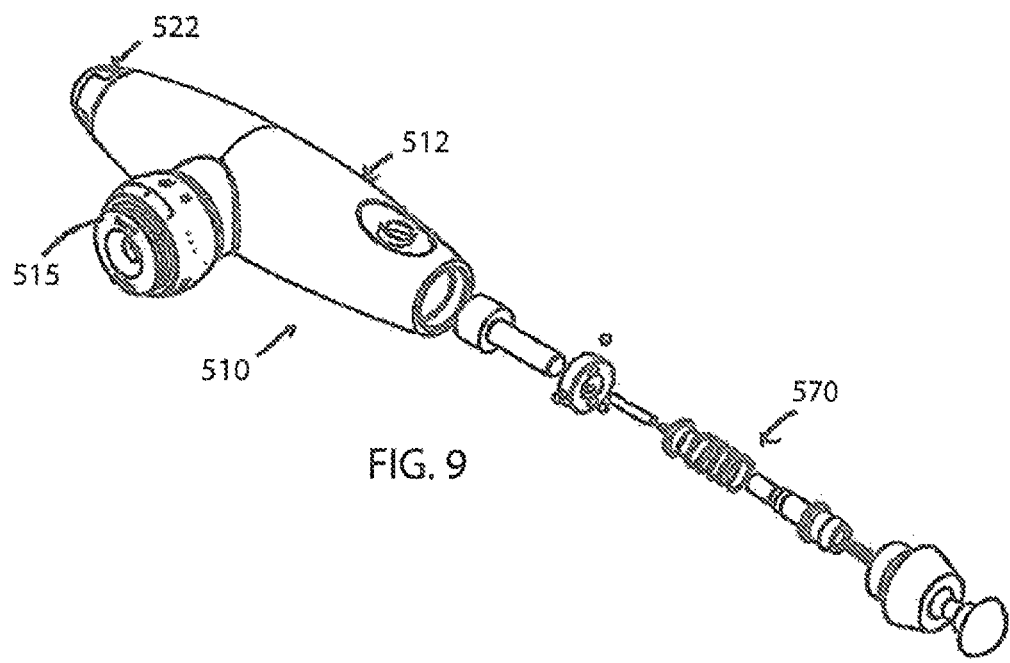
FIG. 9 is an exploded, isometric view of a fourth embodiment of an electronic driving tool constructed according to the present disclosure.

Looking now at FIG. 9, a fourth embodiment of the wrench 510 is illustrated. In the wrench 510, the body 512, in addition to the ratcheting mechanism 515 and other components, such as the power source and electronics unit (not shown), has a pop-out torque level indication mechanism 570, such as that disclosed in U.S. patent application Ser. No. 12/192,295, incorporated herein by reference in its entirety. The pop-out indication mechanism 570 operates in conjunction with the display 522 to illustrate the particular torque level at which the wrench 510 is being operated.

Figure 10:
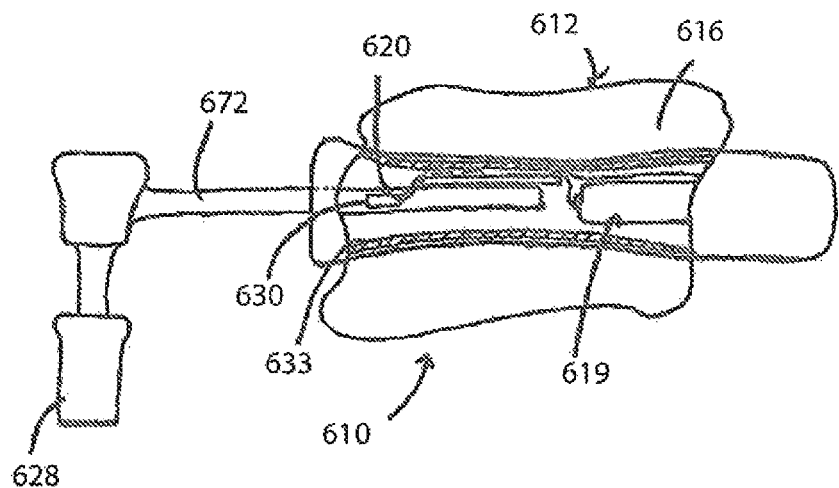
FIG. 10 is a cross-sectional view of a fifth embodiment of an electronic driving tool constructed according to the present disclosure.

Referring now to FIG. 10, a fifth embodiment of the wrench 610 is illustrated in which the wrench 610 is a deflection beam type wrench. The wrench 610 includes a body 612 within which the power source 619 and electronic unit 620 are disposed. A sensor 630 operably connected to the electronics unit 620 is disposed on a beam 672 engaged with the body 612, and having an adapter 628 attached thereto opposite the body 612. The adapter 628 is operable engagable with the fastener via an attachment releasable secured to the adapter 628 in order to allow the wrench 610 to drive the fastener. The torque applied to the fastener by the wrench 610 is measured by the electronics unit 620 via signals received from the sensor 630 as a result of the deflection of the beam 672.

Looking now at FIGS. 11A-13, one embodiment of the display 22 for the wrench 10 is illustrated. The display 22 can take any suitable form, and can be positioned on the exterior surface of the body 12 for interaction with the individual utilizing the wrench 10, or can be disposed within the body 12 in an easily viewable location, such as under a transparent section of the body. The display 22 provides various indications to the user of the wrench 10 regarding the operation of the wrench 10, such as, but not limited to, the actual torque being applied in various units, the amount of torque being applied relative to preset maximum and minimum values, the power level remaining in the power source 19, and any error message with regard to the operation of the wrench 10, e.g., a defect in the operation of the electronic unit 20.

The display 22 can also include one or more user input devices 80 disposed in the body 12. The devices 80 can include a power button 82, a unit selection button 84, increment/decrement buttons 86a and 86b, and three light emitting diodes (LEDs) 88a, 88b and 88c. In one embodiment, the light emitting diodes 88a, 88b and 88c are green, yellow and red, respectively, when activated in response to the torque levels sensed by the electronics unit 20. Also, a speaker 90 for audible signals can also be disposed on the body 12. Additionally, though LEDs 88a-88c and speaker 90 are shown, the wrench 10 may alternatively or additionally include a device for creating tactile sensation such as a vibration, heating, or cooling. Also, though one possible positioning for the display 22 is shown in FIGS. 1 and 2, other locations, such as at the end or underside of the body 12 are suitable as well.

Figure 11A:
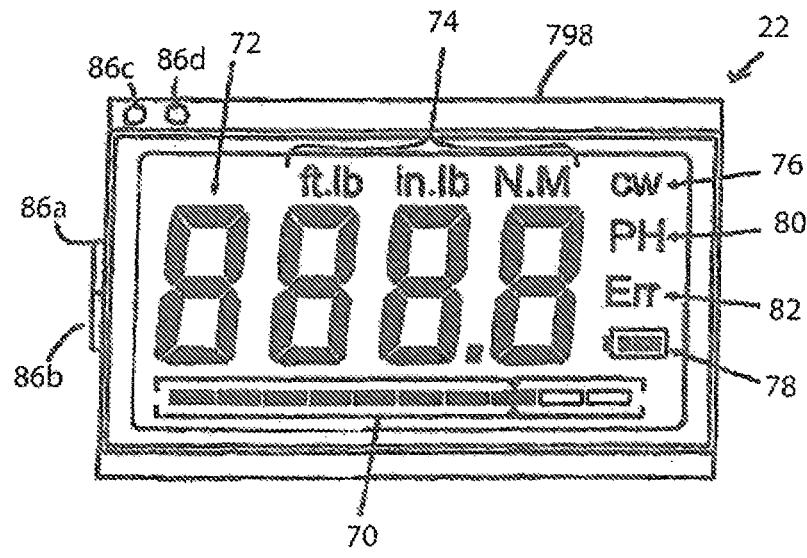
FIGS. 11A-11B are front plan views of the display for the tool of FIG. 1.
Figure 11B:
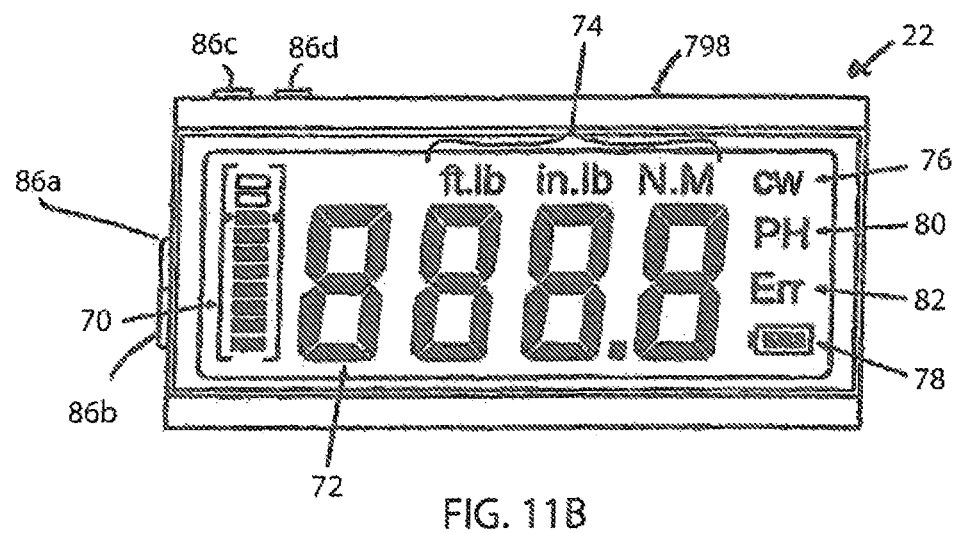
Figure 12:
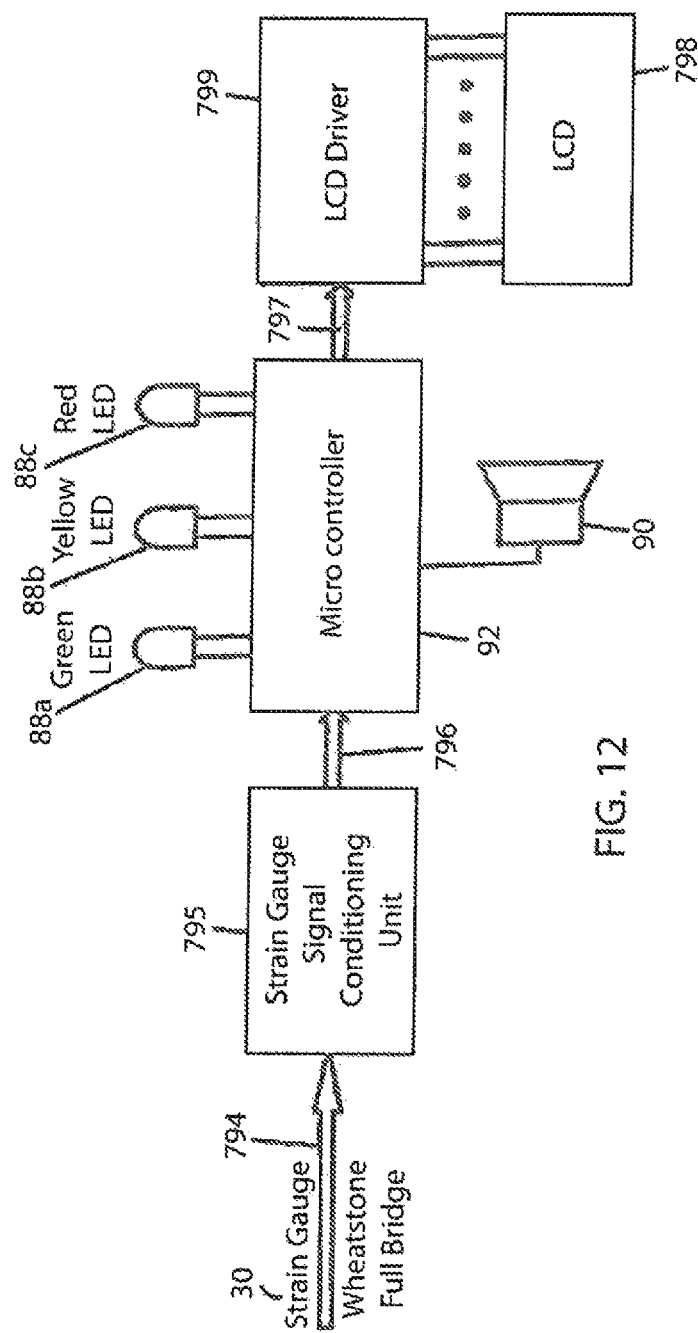
FIG. 12 is a schematic view of a first embodiment of an electronics system of the tool of FIG. 1.
Figure 13:
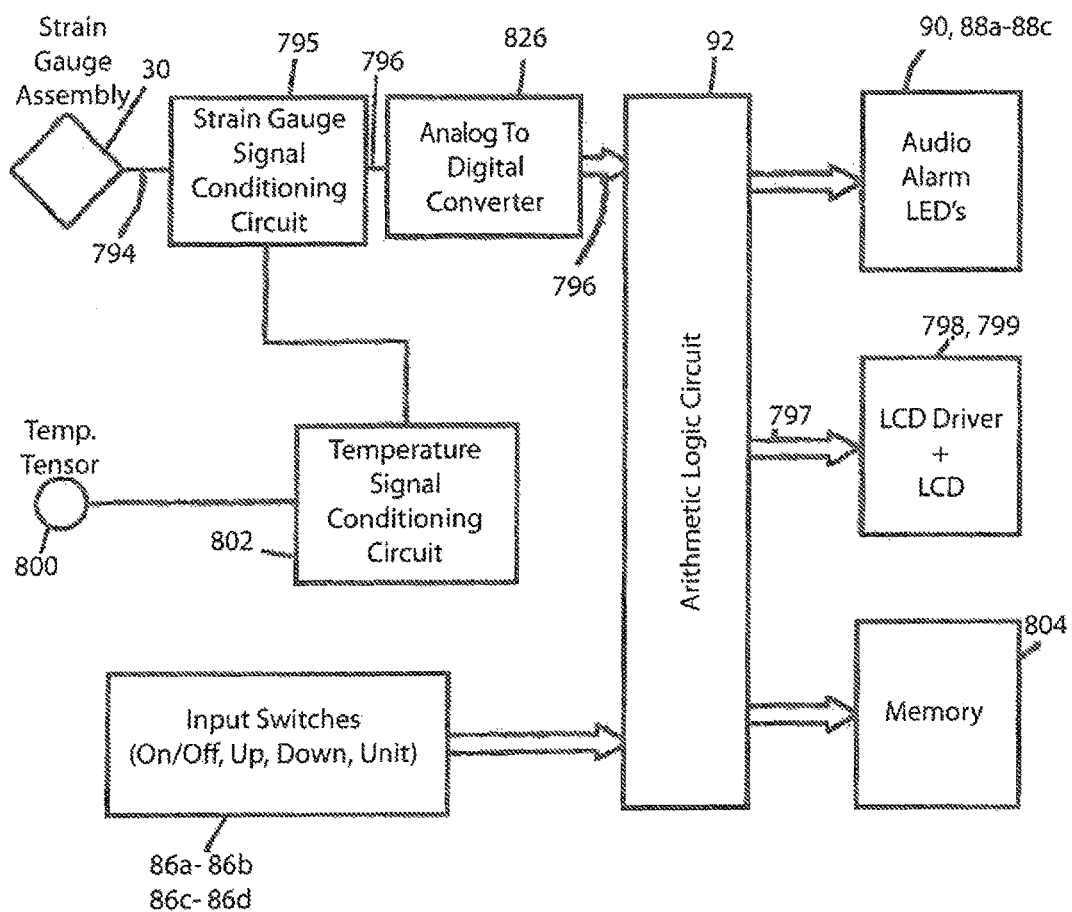
FIG. 13 is a schematic view of a second embodiment of an electronics system of the tool of FIG. 1.

Block diagram representations of the electronics of the wrench 10, including the display 22 and a microcontroller 92, showing various inputs and outputs, are shown in FIGS. 12-13. When electronic torque wrench 10 is used to apply and measure torque, the sensor 30, i.e., the Hall sensor, the piezoelectric sensor, the strain gages of the strain tensor, or other suitable sensing device, sense the torque applied to the fastener and send a proportional electrical signal 794 to a signal conditioning unit 795 that amplifies the signal, adjusts for any offset of the signal, and compensates the signal for the current temperature using temperature sensor 800 and conditioning circuit 802 and adjusting for the offset of the signal increases the accuracy of the wrench by compensating the signal for any reading that may be present before torque is actually applied to the fastener. An amplified and conditioned electrical signal 796 is then fed to the microcontroller 92 that converts electrical signal 796 to an equivalent torque value in the desired units. Microcontroller 92 sends an electrical signal 797 including the current torque level value and the peak torque value to the display 22, which can include a liquid crystal display (LCD) unit 798, via an LCD driver circuit 799. In one embodiment, the display 22 represents the current torque level value as a bar graph and simultaneously displays the peak torque value as a numeric value, as seen in FIGS. 11A and 11B. Furthermore, microcontroller 92 generates alarm signals in the form of one or more audio signals and/or light displays of appropriate color once the current torque level value is within a pre-selected range of the preset limit torque value, that are used to operate the LEDs 88a-88c, and the speaker 90. The LEDs 88a-88c coincide with the level of torque being applied relative to the preset maximum torque level. When any of the LEDs 88a-88c are activated, either in a flashing or continuous manner, the user is alerted as to the level of torque being applied via the wrench 10, with the yellow and red LEDs 88b and 88c, along with the speaker 90 and any associated vibration generator (not shown) indicating to the user that they are approaching or at the torque level where they are over-torquing the fastener.

The switches or buttons 86a-86b are located on the body 12 adjacent the display 22 and enable the user to adjust the parameters utilized by the electronics unit 20 in setting the minimums and maximum torque levels for the wrench 10.

In addition, the electronics unit 20 can include a memory component 800 that is operably connected to the microprocessor or microcontroller 92 in order to record the information received by the unit 92 during the operation of the wrench 10. In one embodiment, torque values are received by microcontroller 92 on a continuous basis over controlled intervals, which may be specified, for example by the operator of wrench 10 through a user interface, such as the buttons 86a-86b, or other devices that can be operably connected to the microprocessor 92. In any case, in another embodiment, one or more torque measurement values are periodically or continuously stored in memory 800 for later retrieval and/or processing.

FIGS. 11A-11B show detailed views of embodiments of digital displays 22 that can be used in any of the embodiments of the wrench 10 of the present invention. The LCD units 798 include a current torque level indicator, a four digit numeric display, an indication of units selected (foot-pound, inch-pound, and Newton-meter), a torque direction indicator (clockwise (CW) by default and counterclockwise (CCW) if selected), a battery level indicator, a peak hold (PH) indicator and an error (Err) indicator. As shown, current torque level indicator is in the form of a bar graph. The bar graph is shown in two embodiments, horizontal and vertical. In either case, preferably, the bar graph includes a total of ten segments and a frame that encompasses all ten segments. The frame is filled by the ten segments when the preset torque value input by the user is reached. At other times, the frame is only partially filled with segments, and therefore gives a graphical display of approximately how much torque is currently being applied and how much more torque needs to be applied to the fastener to reach the preset torque valve.

As shown, two small arrows are located on opposing sides of the eighth segment. The arrows are graphical indicators to the user that the current torque level is above 75% of the preset torque value. Each segment within the frame represents 10% of the preset torque value, starting from the left or bottom of each bar graph, respectively. For example, if only the first two of segments are displayed, the current torque level is above 15% and below 24% of the preset torque value, and is therefore approximately 20% of the preset torque value. Simultaneously, the digital display also displays the peak torque value applied up until that time in the numeric display. As such, if torque has been applied in a continuously increasing manner, the peak torque value displayed will actually be the same as the current torque value. The decimal point will be displayed depending on which units the user has selected.

In use, the user, rather than focusing on four digit numeric display, views the bar graph of current torque level indicator until the applied torque level reaches approximately 75% to 80% of the preset torque value, depending on the user's comfort level when approaching the preset torque level. At this point, the user changes focus to the numeric display for a precise indication of the current torque being applied as the preset torque value is approached. As discussed, the numeric display shows the peak torque value to which the fastener has been subjected. As such, if the user has "backed off" during the application of torque, the value indicated on numeric display will not change until it is exceeded by the current torque value. The display allows the user to apply torque to the fastener and know both how much torque is currently applied and how much more torque needs to be applied before reaching the target preset torque value.

Alternately, the bar graph display can be used for displaying the peak torque value and the numeric display can be used to display the current torque value. Alternate embodiments include graphical displays other than the previously discussed bar graph, such as a pie chart display in which each of five segments represents approximately 20% of the preset torque value initially selected by the user, a circular dial-type display in which each segment also represents approximately 20% of the preset torque value, an indicator mark at approximately 80% of the preset torque value, or a graphical display that is similar in appearance to a standard dial type analog display wherein a pointer, or needle, indicates the percentage of the preset torque value being applied as it points to graduations positioned about the display. Note, although the number of segments and graduations are shown as representing 20% of the preset torque value, the number may be altered as necessary to indicate a different desired percentage of the preset torque value.

Figure 14:
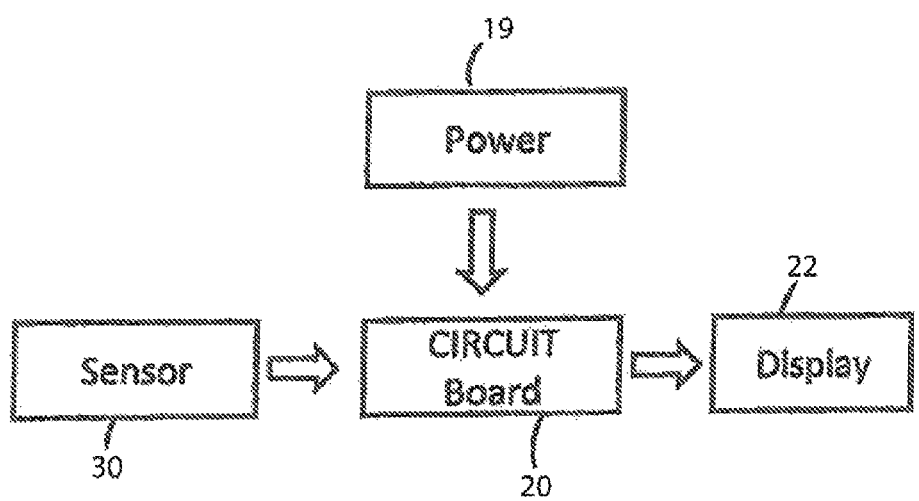
FIG. 14 is a schematic view of a first embodiment of the operating functions of the tool of FIG. 1.
Figure 15:
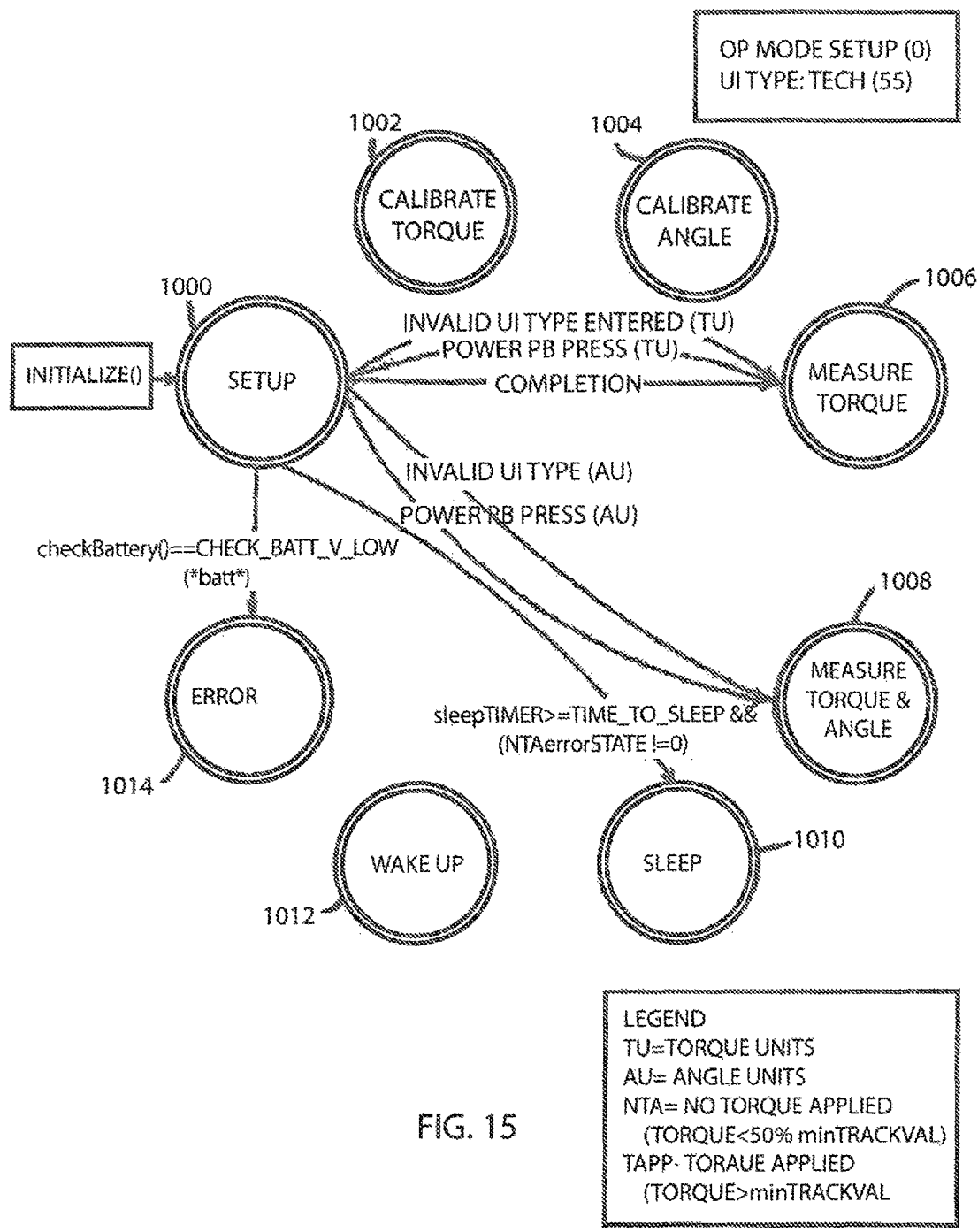
FIG. 15 is a schematic view of a second embodiment of the operating functions of the tool of FIG. 1.

Referring now to FIG. 14-15, the overall functionality of the electronics unit 20 is graphically illustrated. In FIG. 14, in its general functionality, the power supply 19 provides power to the circuit board or electronics unit 20 which receives signals from the sensor 30 for ultimate transmission to the display 22. In FIG. 15, the various functions of the electronics unit 20 are illustrated, namely, an initialization/setup function 1000, a torque calibration function 1002, an angle calibration function 1004, a torque measurement function 1006, a torque and angle measuring function 1008, a sleep function 1010, and wake up function 1012, and an error function 1014.

Figure 16:
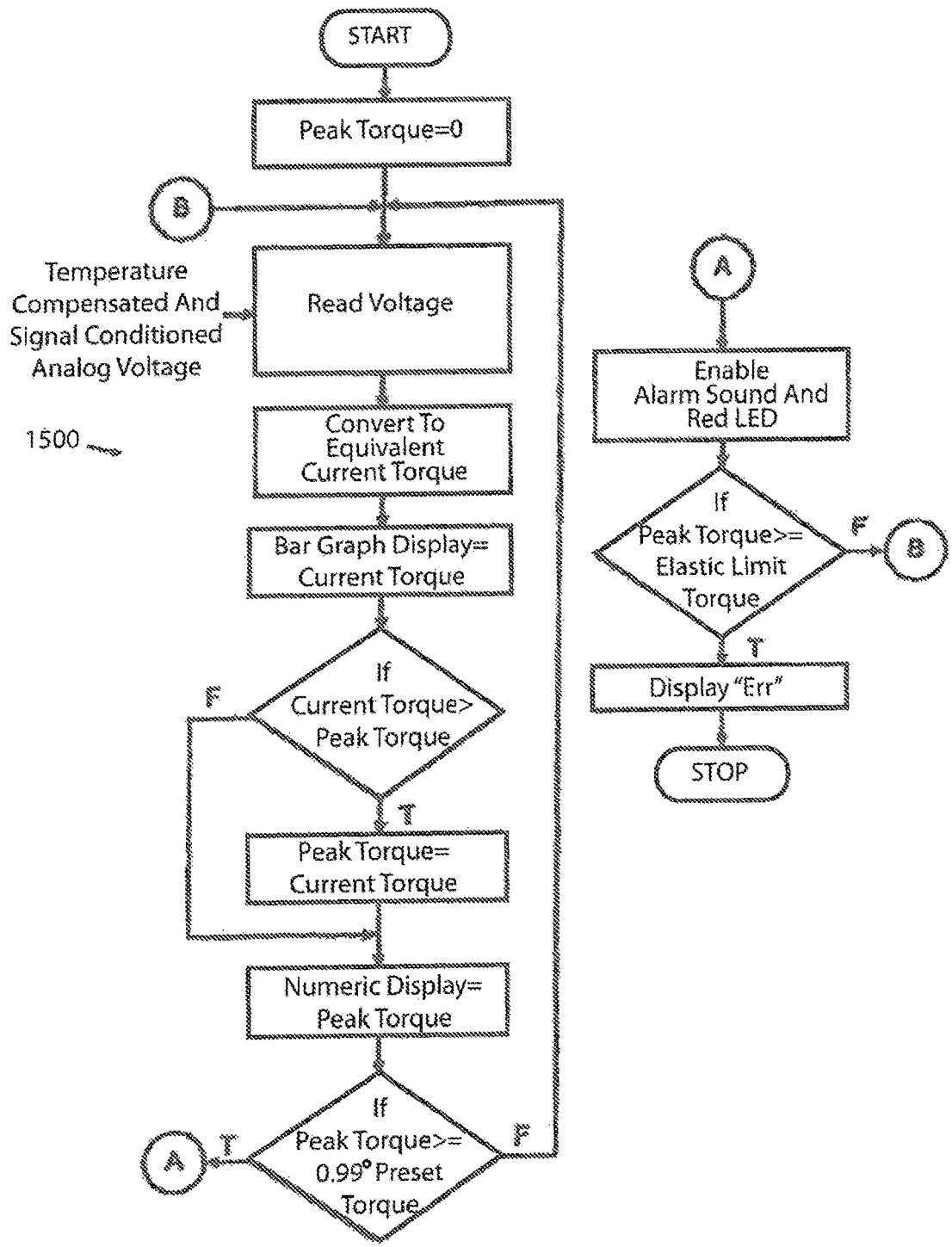
FIG. 16 is a schematic view illustrating the operation of the tool of FIG. 1.

In FIG. 16, a flow chart 1500 of one embodiment of an algorithm using any known and suitable method or system for electronically determining the torque applied by the wrench that can be used with the electronics unit 20 of the various embodiments of the wrench 10, 2000, 4000, 5000, 6000, 7000 of the present disclosure is shown. Prior to initiating torquing operations, a user inputs a preset torque value into the electronic torque wrench that equals the maximum desired torque to be applied to the fastener. This value is displayed in the display 22 until the user actually applies torque to the fastener, at which time the numeric display switches to displaying the peak torque value. As torque is applied, microcontroller 92 receives and reads a temperature compensated and signal conditioned analog voltage signal 796 from signal conditioning circuit 795, converts the analog signal to an equivalent digital number, converts the digital number to an equivalent current torque value corresponding to the user selected units, and determines whether the current torque value is a new peak torque value. This is accomplished by comparing the current torque value to the existing peak torque value, and either replacing the peak torque value if it is exceeded (T), or letting it remain if it is not (F). Once both the current torque value and peak torque value are determined, microcontroller 92 sends electrical signal commands to LCD driver circuit 799 to generate appropriate signals to display 22 for updating the readout shown in current torque level indicator and the peak torque value shown in display 22.

In addition, microcontroller 92 switches green 88a, yellow 88b, and red 88c LEDs on or off depending on the peak torque value applied to the fastener up until that time. Preferably, green LED 88a comes on as long as the peak torque value is below 75% of the preset torque value and is switched off once the peak torque reaches 75% of the preset torque value. Yellow LED 88b comes on for peak torque values greater than 75% but less than 99% of the preset torque value. Red LED 88c comes on once the peak torque value reaches 99% of the preset torque value and stays on thereafter. The selection of percentage ranges for each color may be programmed, and the percentages at which the LEDs are switched on or off can be changed to suit the specific application. Embodiments are envisioned that include a liquid crystal display device that is capable of displaying multiple colors. This permits the warning LEDs to be replaced by appropriately colored symbols on the LCD. As well, the segments of the bar graphs and graphical displays can be made to have varying colors in order to enhance the warning capabilities for the user.

Once the peak torque reaches the preset torque value, or is within a user selected range, microcontroller 92 generates electrical signals to generate an alarm sound on speaker 90. A red color backlight (not shown) coincides with the audible alarm signal, indicating that the preset torque value has been reached. More colors can be added as backlights to further assist the user when approaching the preset torque value. The user is also alerted if the mechanically safe torque value (elastic limit of the strain tensor) has been exceeded, possibly causing the torque wrench to lose proper calibration. This is determined by comparing the peak torque value to the elastic limit torque of the torque wrench. If the safe torque value is exceeded (T), an "Err" message is displayed on error indicator and the unit stops, thus indicating that the electronic torque wrench unit needs calibration before it can be used again.

Figure 17:
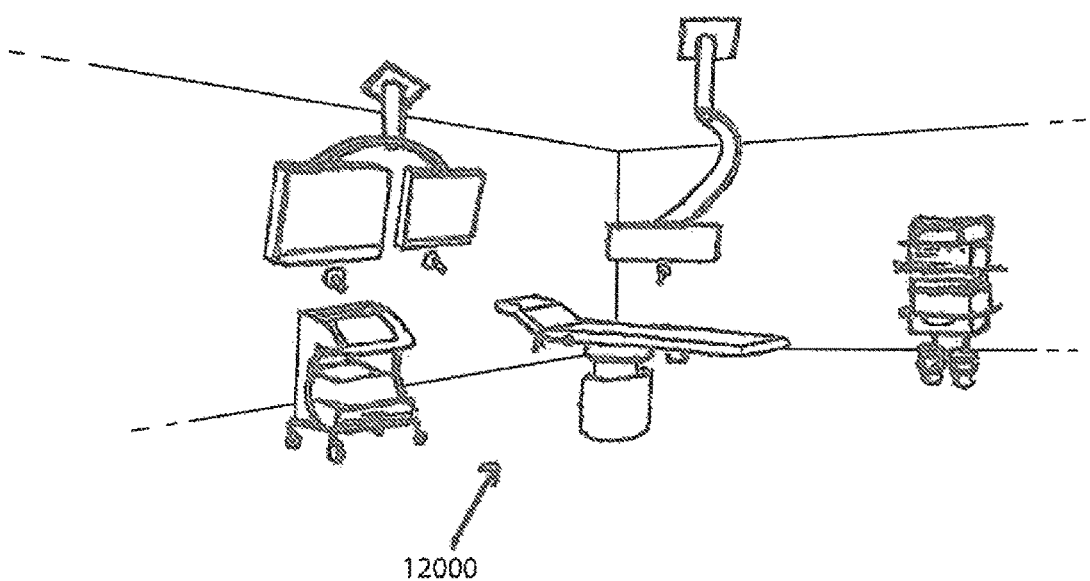
FIG. 17 is a schematic view of a medical suite including a sixth embodiment of an electronic driving tool constructed according to the present disclosure.
Figure 18:
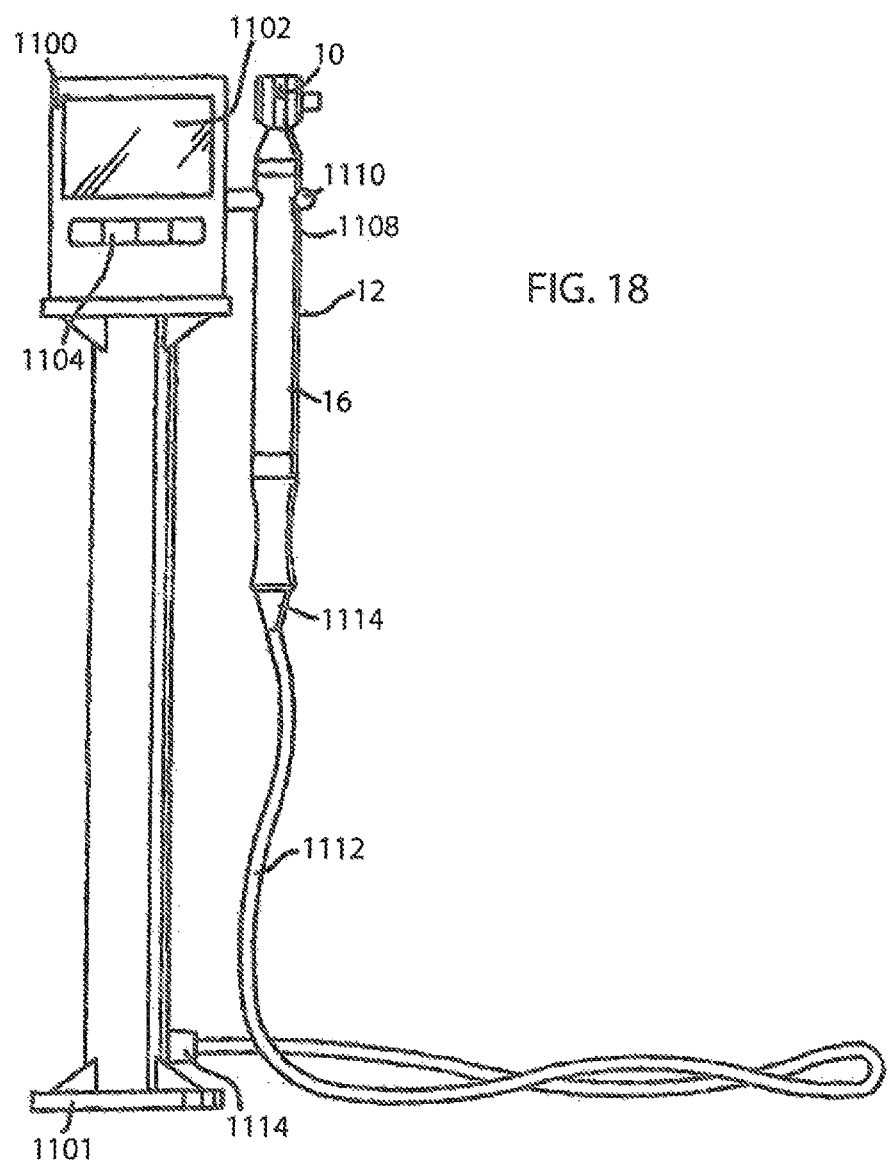
FIG. 18 is a schematic view of the tool of FIG. 17.

As shown in FIGS. 17-18, the wrench 10 can be configured for use in a medical suite 12000 to mate with a control unit 1100. Control unit 1100 is configured to communicate with wrench 10 when wrench 10 is docked therein or otherwise engaged therewith. Control unit 1100 include control unit display 1102, control unit buttons 1104 used for inputting commands and interfacing with menus presented on display 1102, and docking section 1106. During docking, wrench 10 is inserted in docking cavity 1108 defined by cradle 1110 and having a width dimension, a length dimension, and a depth dimension which are slightly larger than a corresponding length, width, and depth of body 12 to allow removably secure positioning of wrench 10 within the docking cavity 1108. A coupling or junction (not shown) is also provided along an interior wall of docking cavity 1108 for electrically connecting control unit 1100 to microcontroller 92 in the body 12. Connection between the control unit 1100 and wrench 10 may also be via wireless communication when control unit 1100 and wrench 10 are brought in close proximity.

Control units may also be commonly available portable digital assistants or PDA such as those available from Palm, or other mobile computing devices, including various tablet computers and smart phones, among others. Software configured to communicate with wrench 10 may be loaded onto the PDA which can use operating systems such as Palm OS, Microsoft Windows CE, or other mobile computing device operating systems presently available or hereafter devised. The communications and operations protocols used by the tool may also be written in HTML or XML programming language, or other suitable systems presently available or hereafter devised for interoperability with a wide range of software and hardware platforms.

The control unit 1100 can be in the form of an Ethernet cradle which is similar to the cradle bundled with most hand held devices. However, such an Ethernet cradle may be designed to include an Ethernet card and an RJ-45 connector. This connector allows the unit to connect to a local area network via a CAT5 cable attached to a hub or switch. This will allow for rapid communication (10 Mbps, 100 MBps, or gigabit) between the wrench 10 and a tool management system 1200.

Figure 19A:
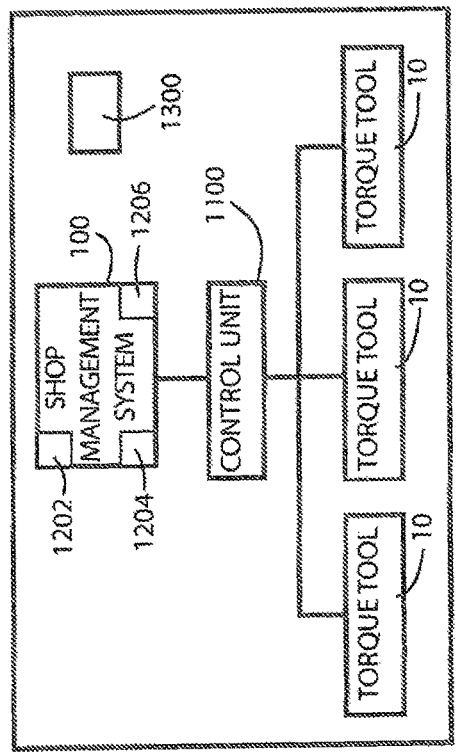
FIGS. 19A and 19B are schematic views illustrating the operation of the tool of FIG. 17.
Figure 19B:
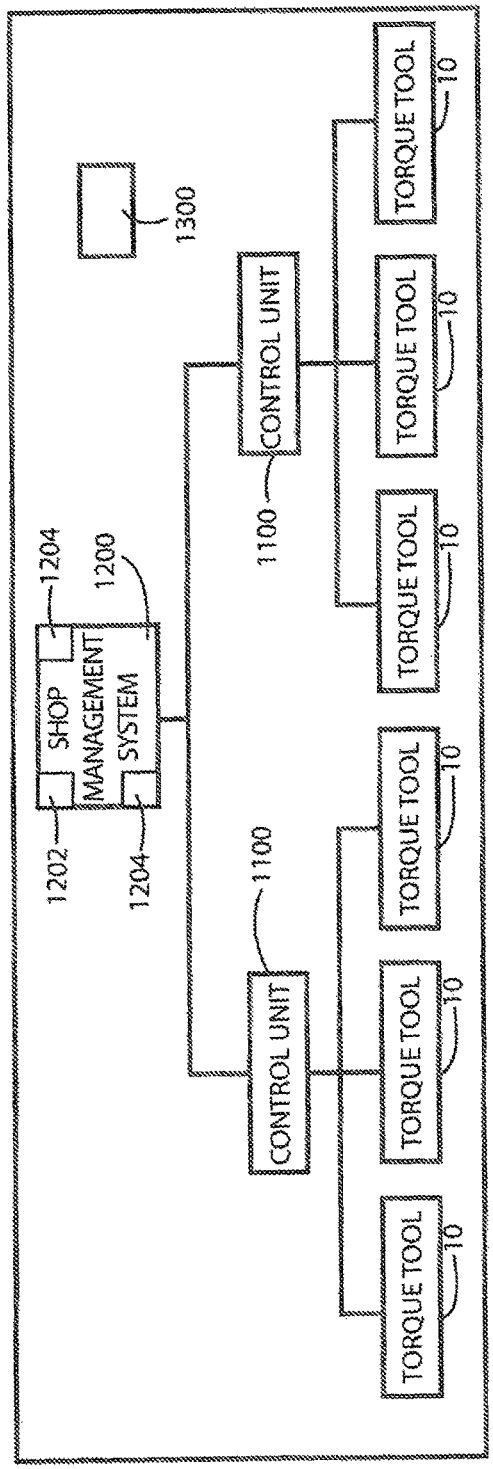

FIGS. 19A-19B are simplified diagrammatic views of a tool management system 1200. Tool management system 1200 can be configured on a general purpose computer that includes a processor 1202, a specification database module 1204 accessible by or loaded onto the system 1200, a database module 1206 accessible by or loaded onto system 1200, and a communications port 1208. The modules 1204, 1206 can be accessed by the processor locally or remotely over a communications network such as a local area network, wide area network, over an intranet, or over the Internet or another suitable communications hereafter devised and usable for this system. Tool management system 1200 will also include both dynamic memory such as RAM and a storage device such as a hard drive or the like. The term "module" referenced in this disclosure is meant to broadly cover various types of software code including but not limited to routines, functions, objects, libraries, classes, members, packages, procedures, methods, or lines of code together performing similar functionality to these types of coding, therefore one program can operate to provides the functionality, or the functionality can be divided over a number of programs, accessible either locally or remotely. The system 1200 may also communicate with one or more output devices 1300 such as monitors or printers. For the purposes of the present example, and as illustrated in figures, the database modules 1204, 1206 will be loaded on the tool management system 1200.

The tool management system 1200 can communicate directly with wrench 10. System 1200 and wrench 10 make up torque management system. This connection may be via a hardwired or wireless using any of the communications protocols previously described. In an alternative embodiment, the control unit 1200 can also be used an intermediate interface between tool management system 1200 and wrench 10 to form the torque management system 1400. The control unit 1100 can also be used to control more than one wrench 10. Recall that wrench 10 removably docks with control unit 1100 so one wrench 10 can be removed and another connected so that one control unit 1100 can be used to communicate with more than one wrench 10.

The general steps by which tool/torque management system 1200/1400 are used initially involve the identification of a torque application, can be any task or process that requires the use of a torque tool where precise tolerances, a desired range, or limits of the magnitude of the torque applied need to be monitored. Generally, a fastening or unfastening of a fastener to a member can be a torque application. One specific example of a torque application is related to inserting screws into a plate in a human body during a surgical procedure. In this example, a number of screws need to be inserted through the plate into bone in order to secure the plate where desired within the body, e.g., to repair a break in a bone. It is known in the medical device/fastener industry that each manufacturer offers specifications for a recommended and maximum safe amount of torque that should be applied to securely fasten the screws.

Once selected, the information on the torque application is supplied from a database 1204, 1206 on the system 1200 to the wrench 10, and/or to the control unit 1100. In doing so, the system 1200 references the specifications database module 1206 to find corresponding manufacturer's specifications for the identified torque application. Alternatively, the fastener (not shown) can have a code used to identify the fastener with system 1200. The identification to the system 1200 can be made via the wrench 10, the system 1200, or the control unit 110 using any input method or device including using a keyboard, interacting with a graphical user interface that has menus or other selection protocols, scanning a barcode, or from import/export or other communication with procedure database.

Once identified, the manufacturer's specifications for the identified torque application are retrieved to the wrench 10. If the system 1200 referenced the specification database 1206, then the specifications are transmitted from the system 1200 to the wrench 10 via a communications path. Alternatively, the system 1200 sends the specifications to the control unit 1100 which in turn transmits the specifications to the wrench 10 when the wrench 10 is docked therein. If the specifications are already on wrench 10, for example because the same torque application was performed prior to the current torque application, the specification can be recalled from the memory 800 of the wrench 10. Similarly, if the specifications are already resident on the control unit 1100, the specifications can be recalled and loaded onto wrench 10.

After loading the specifications on the wrench 10, a user or operator, such as, for example, physician, uses the wrench 10 loaded with the torque application specifications to perform the torque application. The wrench 10 or the wrench 10-control unit 1100 combination are configured to guide the user through the torque application. This guidance can come in the form of specifying a particular portion of the application and displaying a maximum allowable applied torque. The torque magnitudes displayed can be in either U.S. customary units (lbs-ft) or in S.I. units (N-m). The guidance can also come in the form of producing an alert during torque application to notify the user that the user is approaching or has exceeded a specification, such as the LEDs 88a-88c, the speaker 90 or other devices mentioned previously.

Generally simultaneously with the guidance process described above and the various steps of the torque application, a torque sensing device within the wrench 10 measures or captures data corresponding to the actual torque applied for that application. That information or data is stored in memory 800 within the wrench 10 or is immediately transmitted back to the control unit 1100 or directly to the tool management system 1200. The data is used to create a record of exactly how much torque was applied during the various stages of the torque application, and how long the wrench 10 was in use. In an embodiment where the data is not immediately transmitted from the wrench 10, the data can be retrieved and sent to the control unit 1100 and system 1200 during docking.

The specifications and other torque-related information in the specifications database module 1204 can be compiled from promulgated industry standards or from specification released by original equipment manufacturers. For example, factory torque specifications developed by the device manufacturer relating to the proper torque for tightening the fasteners can be maintained in the database 1204. The information can be modified, updated and corrected as necessary. If this system 1200 is connected to a network that has access to updated specifications, this information update can occur at generally any time of the day.

This information recorded by the system 1200 can be used to determine the number of uses of a particular wrench or tool, such that the system 1200 can inform the user that the tool must be replaced or that a component of the tool, such as a power/sensor pack 2004 (FIG. 25) needs to be discarded and replaced. The system 1200, when incorporated at least partially into the pack 2004 can provide an indication to the user of the current status of the tool, such as how long in terms of minutes or hours, or how many uses the tool or component thereof has left prior to the need for replacement.

Figure 26:
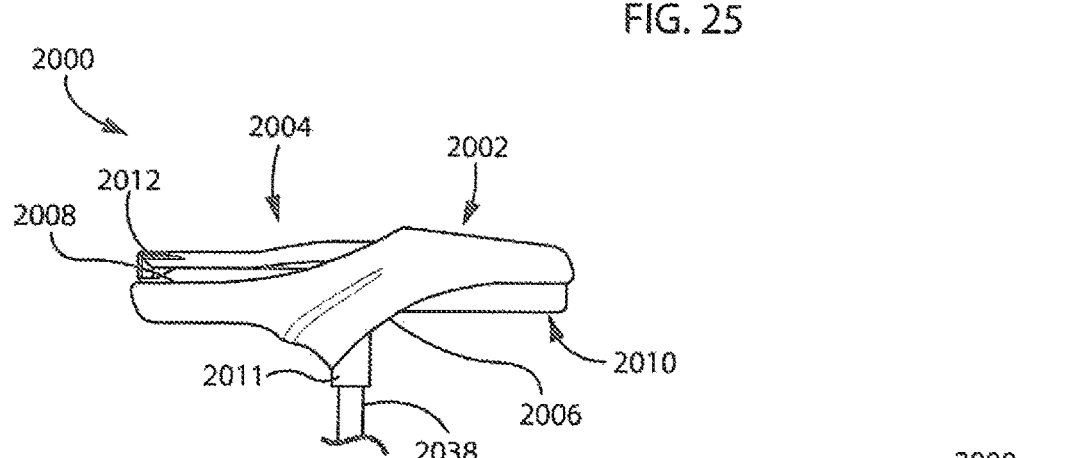
FIG. 26 is a front plan view of the tool of FIG. 25.

In addition, surgical torque wrenches and similar surgical devices are recommended to be sent back to the factory for calibration after a period of time which is usually six months to a year since date of manufacture. However, in reality these wrenches are sometimes not checked to ensure they are calibrated or properly maintained. In the tool 2000 as shown in FIG. 26, the tool 2000 can have sensors or other electronic components on or within the tool 2000 that keep track of the usage and age of the tool 2000 to help make the device smarter and inform the user when it is time to send the tool 2000 for service and calibration. Some examples of these types of sensors to be used alone or in combination with one another include:

1. A thermal sensor and counter type circuit (not shown) can be employed within the tool 2000, such as in conjunction with the electronics unit 20, to count the number of autoclave cycles and alarm or otherwise notify the user when the preprogrammed number of cycles has been reached that the tool 2000 needs to be serviced or have its calibration checked, such as via the display 22, 6000, 6002.
2. A sensor (not shown) used in conjunction with the electronics unit 20 can count the number of actuations of the tool 2000 and notify the user via the display 22, 6000, 6002 when the preprogrammed number of actuations has been reached that the tool 2000 needs to be serviced or have its calibration checked.
3. Electronic components like real-time clocks can be employed in conjunction with the electronics unit 20 to keep track of time the tool 2000 has been in the field since date of its manufacture. The clock can be programmed to send out a signal or message to notify the user, such as via the display 22, 6000, 6002, that it is time for the tool 2000 to be calibrated or serviced. The clock could be reset or reprogrammed for the next calibration interval after the calibration service has been performed.

Alternatively, the tool 2000 can be supplied with a counter and an electronic storage medium or memory device (not shown) within the tool 2000 in conjunction with the electronics unit 20 to give an indication of how much time the tool 2000 has been in use. This information that is sensed and/or stored by the tool 2000 can include 1. How many times the tool 2000 has been autoclaved or
2. The number of times the tool 2000 had been actuated.
3. The torque values that have been applied, especially when the tool 2000 has been torqued excessively.
4. The age of the tool 2000 since date of manufacture.

This information is stored in the electronic memory medium 800 in the tool 2000 or in a separate electronic storage location (not shown) operably connected to the tool 2000 directly or wirelessly, and this data could be retrieved at any time by simply scanning the tool 2000 with a scanner. In the case of tools 2000 with a screen 6000, the tool 2000 could display a message or alarm on the screen to inform the user when it is time to send the tool 2000 for calibration or service or advise the user how much life is left on the tool 2000.

In order to maintain system integrity and security, the various steps and/or operations described above may include password system implementation or user authentication for added security and user accountability. For example, a physician performing a torque application may have to enter a worker 1D. As another example, specifications updates to the specification database module 1204 may require manager level access.

Figure 20:
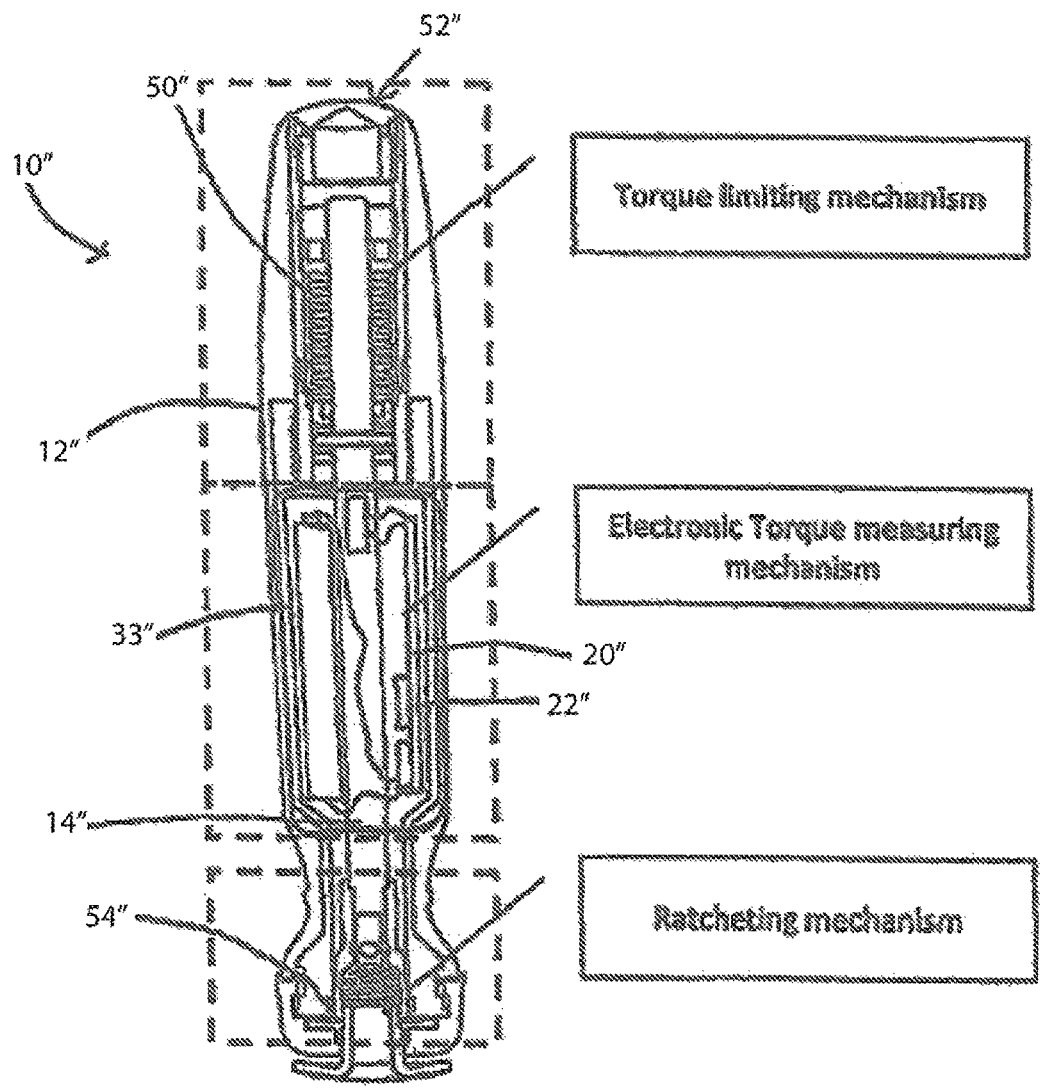
FIG. 20 is a cross-sectional view of a seventh embodiment of an electronic driving tool constructed according to the present disclosure.

Looking now at FIG. 20, a seventh embodiment of the present invention is illustrated in which the electronic torque wrench 10" includes a wrench body 12", a ratchet/wrench shaft 14", and a battery assembly 19", and an electronics unit 20" with a user interface or display 22" disposed within a suitable barrier 33" formed by or within the body 12" and engaged with a sensor 30" on the shaft 14". A torque limiting mechanism 50", such as that disclosed in U.S. Pat. No. 7,430,945, which expressly is incorporated herein by reference in its entirety, is disposed within and at one end 52" of the wrench body 12", and a ratcheting mechanism 54" is located opposite the mechanism 50", with both mechanisms 50" and 54" operably connected to the shaft 14".

Figure 21:
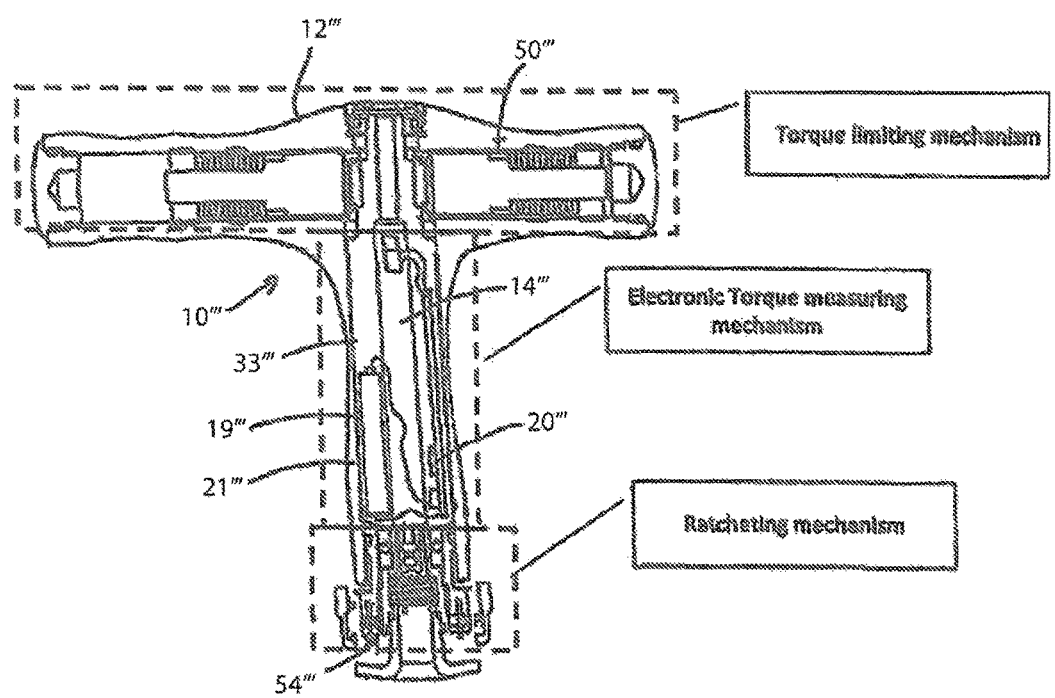
FIG. 21 is a cross-sectional view of an eighth embodiment of an electronic driving tool constructed according to the present disclosure.

Referring now to FIG. 21, an eighth embodiment of the present invention is illustrated where the wrench 10''' has a T-shape, with the shaft 14''' extending perpendicularly from the body 12'''. In the illustrated embodiment, the shaft 14''' is disposed centrally on the body 12''', such that the battery assembly or power source 19''' and the electronics unit 20''' disposed within a suitable barrier 33''' formed by or within the body 12''' and operably connected to the shaft 14''' via the sensor 30" are disposed around the shaft 14''' within a housing 21''' connected to and extending perpendicularly from the body 12'''. The housing 21''' is connected to the body 12''' and the shaft 14''' can be connected directly to the body 12''' or to a torque limiting mechanism 50''', such as that disclosed in U.S. Pat. No. 7,430,945, which expressly is incorporated herein by reference in its entirety, disposed within the body 12'''. In addition, the disposed at least partially within the housing 21''' and in connection with the shaft 14''' is a ratcheting mechanism 54''' as previously described with regard to the embodiment of FIGS. 1 and 2. Further, in this, or any other embodiment of the wrench 10 the wrench can include a ratcheting mechanism 54, a mechanical torque limiting mechanism 50, or a mechanical torque measuring mechanism, such as the mechanical torque level measuring and/or indication mechanism 570, or any combination thereof in addition to the other components of any disclosed embodiment of the electronic torque wrench 10

Figure 22:
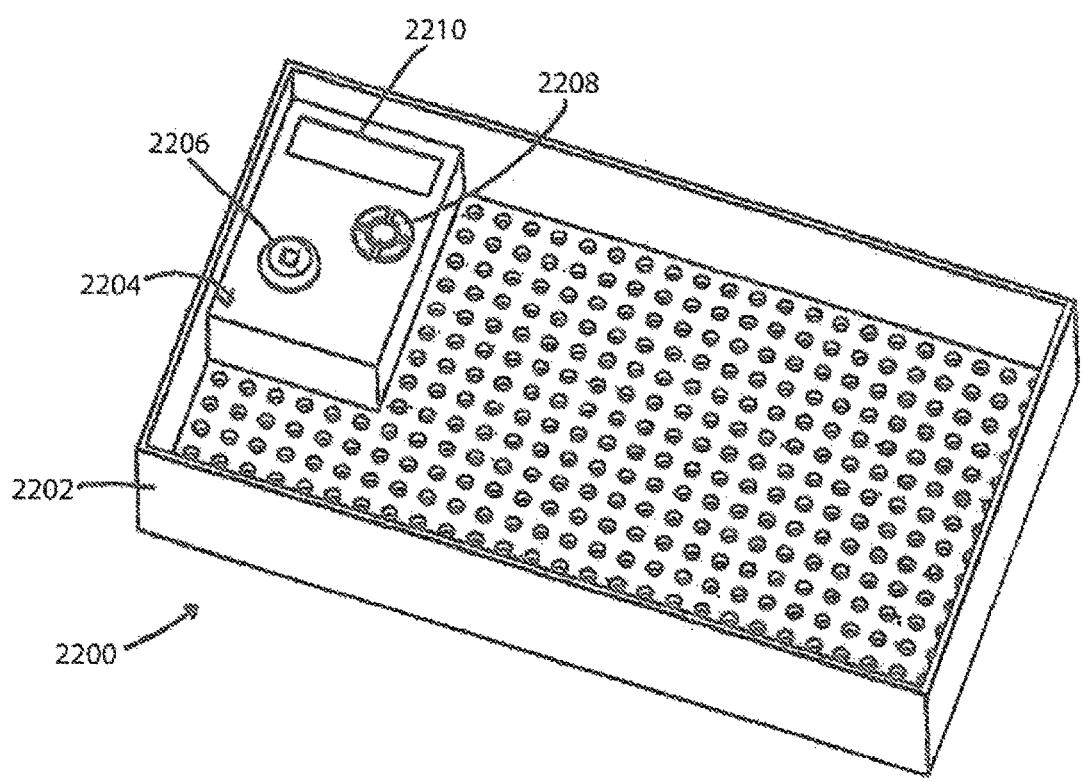
FIG. 22 is an isometric view of a calibration tray used with the electronic driving tool.
Figure 23:
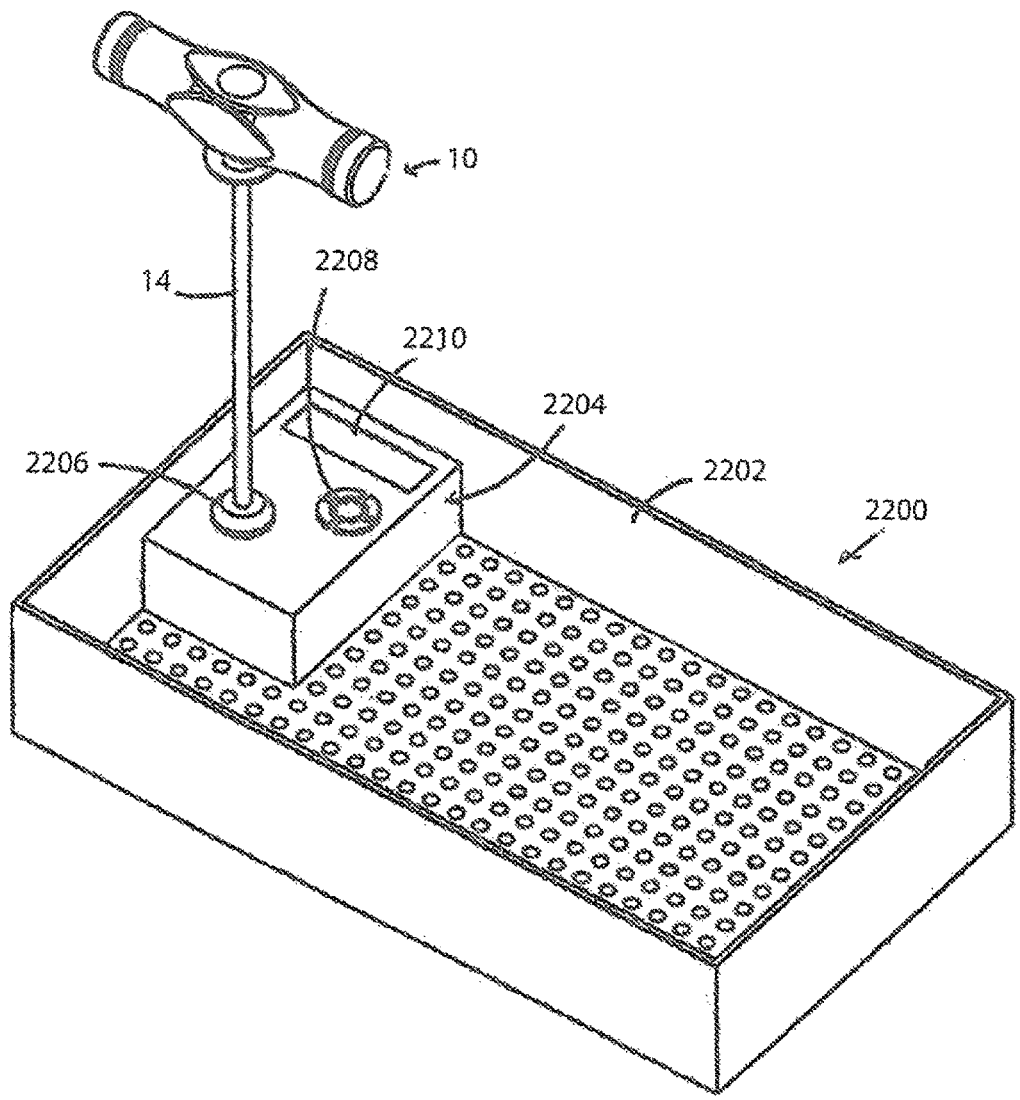
FIG. 23 is an isometric view of a driving tool constructed according to the present disclosure utilized with the calibration tray of FIG. 22.
Figure 24:
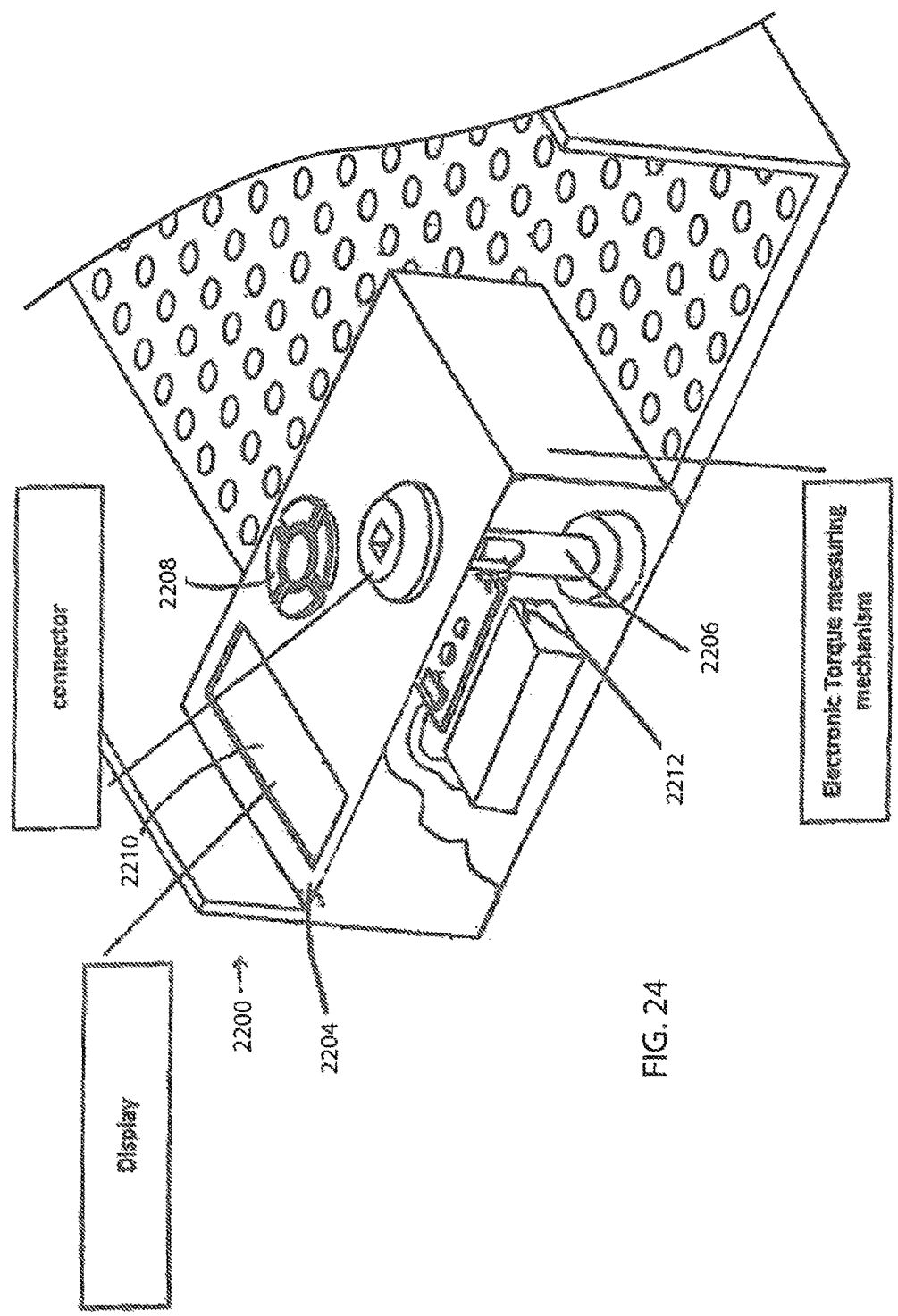
FIG. 24 is a partially broken away, isometric view of the calibration tray of FIG. 22.

Referring now to FIGS. 22-24, a tray 2200 is illustrated for use with the wrench 10 of any embodiment of the present invention. The tray 2200 includes an enclosure 2202 within which the wrench 10 or other tool can be initially packaged, along with other suitable attachments or devices (not shown) for use with the wrench 10. The enclosure 2202 also houses a calibration device 2204 therein. The device 2204 includes a connector port 2206 for engagement with the shaft 14 of the wrench 10, a number of operational buttons 2208 to control the operation of the device 2204, and a display 2210 for providing a visual representation of the output of the device 2204 to the user. The connector 2206 is operably connected to a torque-measuring device 2212 disposed within the device 2204, and capable of determining the torque applied to the connector port 2206 by the wrench 10, and providing an output of the torque value determined via the display 2210. By engaging the wrench 10 with the device 2204 and measuring the torque applied by the wrench 10 on the wrench 10 and on the device 2204, it is possible to determine if the wrench 10 needs any adjustment in order to have the torque level measured by the wrench 10 match the level measured by the device 2204. The tray 2200 can also be formed without the device 2204 and simply used as an easy to assemble receptacle for holding each of the items, including the tool or wrench 10, forming the kit to be in any given procedure or process.

In other alternative embodiments, the battery assembly/power source 19 for the wrench 10 of any embodiment of the present invention can be formed to be removable as a unit from the body 12 of the wrench 10 similarly to the embodiment in FIG. 7. The battery assembly/power source 19 is initially formed as a sterile component that can be secured to or within the body 12 of the wrench 10 to supply power thereto, and optionally to form a part of the barrier 33 or that can be separate from the barrier 33. In circumstances where the wrench 10 is dropped or where the wrench 10 is stored for a significant period of time, the power source 19 can be removed from the wrench 10 and the wrench 10 can be autoclaved. A new, sterile power source 19 can then be engaged with the wrench 10 to provide power to the wrench 10.

Figure 25:
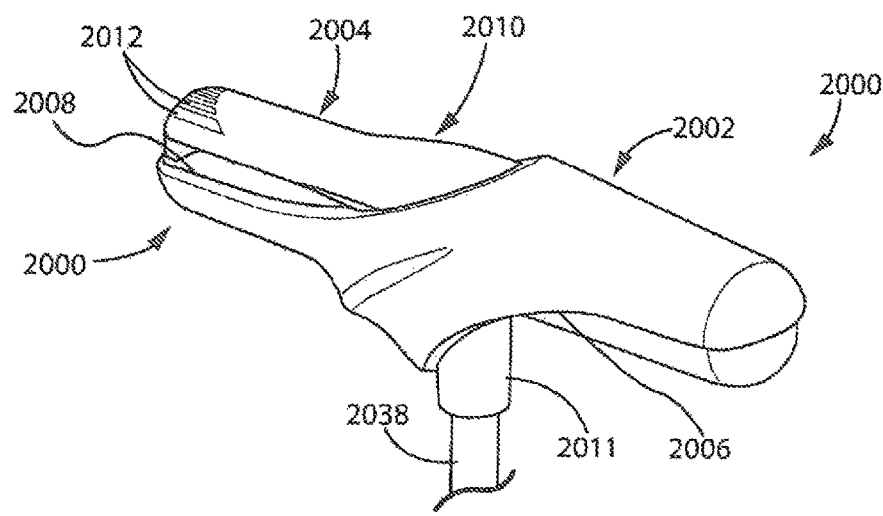
FIG. 25 is a front isometric view of a ninth embodiment of an electronic driving tool constructed according to the present disclosure.
Figure 27:
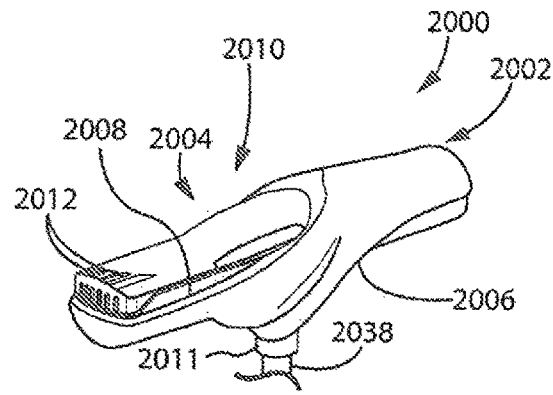
FIG. 27 is a rear isometric view of the tool of FIG. 25.
Figure 30:
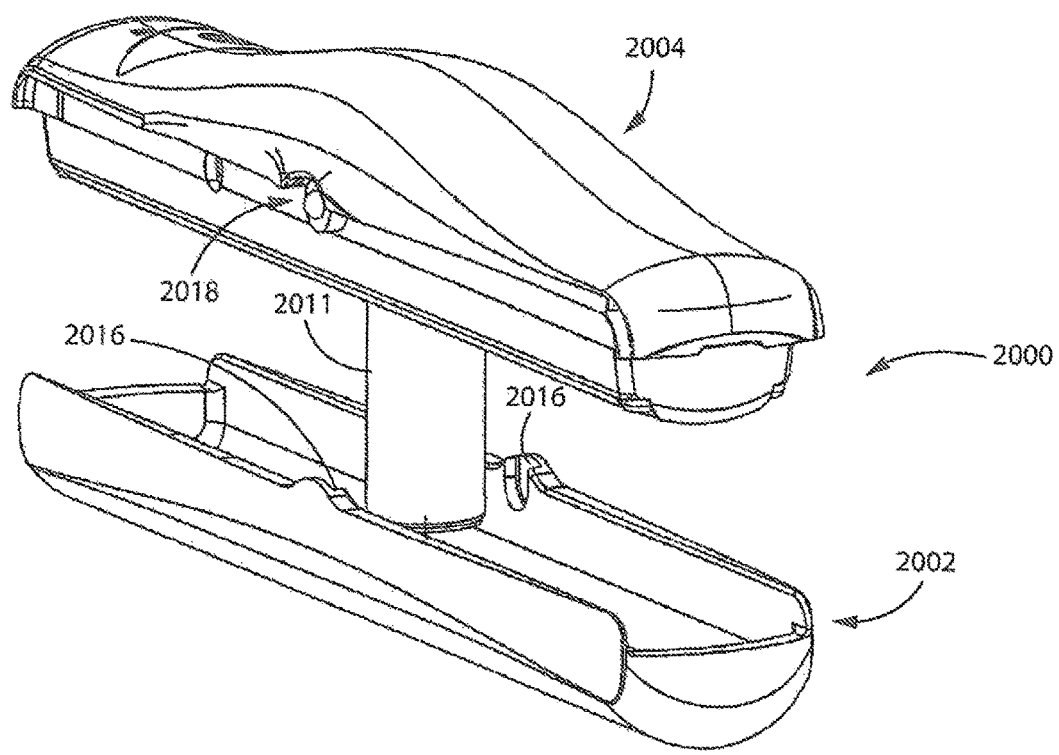
FIG. 30 is an isometric view of a twelfth embodiment of an electronic driving tool constructed according to the present disclosure.
Figure 35:
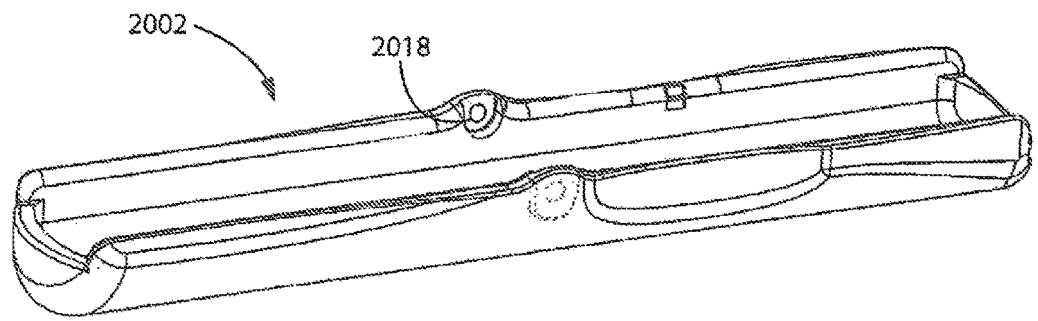
FIG. 35 is an isometric view of the cradle of the tool of FIG. 30.

Looking now at FIG. 25, a ninth embodiment of the electronic driving device 2000 is illustrated. In this embodiment, the device or tool 2000 includes a body or cradle 2002 and a power pack/sensor module 2004. The cradle 2002 is shaped as desired to provide an effective gripping surface for an individual utilizing the tool 2000, and can be formed to have any desired configuration or designs thereon. In the embodiment of FIGS. 25-27, the body or cradle 2002 has a sleeve-like shape with apertures 2006 and 2008 disposed generally opposite one another. The power pack/sensor module 2004 includes a housing 2010 shaped complementary to the shape of the cradle 2002, and has a sleeve 2011 extending outwardly from the housing 2010 that is operably connected to a electronics unit/torque sensing mechanism 2014 within the housing 2010 and adapted to receive and engage an adapter 28, 2052 and/or an implement shaft 2038 for engagement with and driving of a fastener (not shown). The housing 2010 is configured to be slidable or otherwise movable with respect to the cradle 2002 such that the housing 2010 can be inserted within the cradle 2002 by inserting the housing 2010 through the aperture 2006 and pushing the housing 2010 through the cradle 2002 until reaching the opposite end of the aperture 2008. In this position, the visual torque indicators 2012 on the housing 2010 that are operable by an internal power source (not shown) in response to the torque sensed by the torque sensing mechanism 2014 within the housing 2010 are visible through the aperture 2006 and/or 2008.

The following are certain features of the illustrated embodiment of the tool 2000:
  Accuracy of measurement of torque by sensing mechanism 2014 is ±1%
  in one embodiment of the sensing mechanism 2014, the solid state sensor does not rely on mechanical friction, thereby increasing accuracy
  The indicators 2012 in one embodiment are formed as LEDs that are operated sequentially and/or cumulatively to provide visual signals when approaching a torque limit, thus reducing the chance of over torque.
  Other indicators, such as a vibrating motor (not shown) disposed within the housing 2010, and green LED 2012 will notify surgeon that torque set point has been reached.
  Other indicators, such as an audible buzzer, and a red LED 2012 activate to signal over torque.
  The torque sensing mechanism 2014 of the tool 2000 can be calibrated to five (5) set torque points and the user can be notified that the torque set point has been reached by illuminating lights 2012, activating the buzzer or a vibrating motor or a combination thereof.
  The above feedback devices 2012 can also be made to pulse on and off at a varying frequencies. This pulsing would also conserve battery power.
  The housing 2010 can include a light (not shown) to shine through the cradle 2002 or an aperture 2006, 2008 onto the site where the tool 2000 is being applied.
  The light weight design of the cradle 2002 and the housing 2010 of suitable materials, such as selected plastics and metals, is lighter than mechanical torque handles thereby reducing user fatigue.
  The sensor module 2004 provides for a custom programmable torque set point and tolerance band to suit implant design.

The following are some of the advantages of single use design for power pack/sensor module 2004 use with the tool 2000:
  The sensor module 2004 provided for use is in a certified factory calibrated condition.
  The cost for the tool 2000 in a procedure tray 2200 is significantly lower since the majority of the cost is in the disposable sensor module 2004 which is a single use item billed to the surgical procedure.
  The reusable cradle 2002 is of simple construction, such as of a suitable plastic or metal, and therefore easy to clean and sterilize.
  The tool 2000 takes up less room in the procedure tray 2200 and takes weight out of the tray 2200 hence lighter and easier to sterilize the components of the procedure tray 2200.
  The construction of the tool 2000 allows two tools 2000 to be disposed in the procedure tray 2200 to provide redundancy for the tray while still providing a lighter and lower cost tray than a procedure tray 2200 carrying one mechanical reusable handle.
  The tool 2000 eliminates the need for recalibration or maintenance programs, facilities and personnel, as the power pack/sensor module 2004 is pre-calibrated for the single use, and then disposed of.

FIGS. 28A-28B show another embodiment of the tool 2000. In this embodiment, the cradle 2002 and the power pack/sensor module 2004 are formed such that the power pack 2004 is inserted into the cradle 2002 in a top loading fashion, with the sleeve or stem 2011 extending through a central opening 2013 in the cradle 2002. FIGS. 29A-29B show another embodiment of the tool 2000 in which the cradle 2002 is formed with a single aperture 2006 at one end, such that the power pack 2004 is inserted into the cradle 2002 in a side loading fashion, with the stem 2011 extending through a slot (not shown) formed in the cradle 2002.

Looking now at FIGS. 30-35, another embodiment of the tool 2000 is shown in which the cradle 2002 includes locking device 2300 used to hold the module 2004 in the cradle 2002. In the illustrated embodiment, the locking mechanism 2300 includes a number, and preferably a pair of opposed recesses 2016 in the cradle 2002 that are engaged by a locking member 2018 disposed on the housing 2010. The locking member 2018 includes a casing 2020 disposed within the housing 2010 and extending outwardly from opposed sides thereof. The casing 2020 includes a pair of bores 2022 at each end within each of which are disposed a spring 2024 and a detent 2026. The detent 2026 is retained within the bore 2022 by an inwardly extending rim 2027 formed at the outer end of the bore 2022, where the rim has a diameter less than that of the detent 2026. The detents 2026 are urged out of the bores 2022 by the springs 2024. When the housing 2010 is positioned within the cradle 2002, the sides of the cradle 2002 initially press the detents 2026 into the bores 2022 against the bias of the springs 2024. When the detents 2026 reach the recesses 2016, the springs 2024 urge the detents outwardly into the recesses 2016 to secure the housing 2010 to the cradle 2002. Removing the housing 2010 from the cradle 2002 requires a sufficient force be applied to housing 2010 to urge the detents 2026 back into the bores 2022 against the bias of the springs 2024. The force exerted by the springs 2024 is such that the housing 2010 will not be inadvertently removed from the cradle 2002 during the normal operation of the tool 2000.

Figure 36:
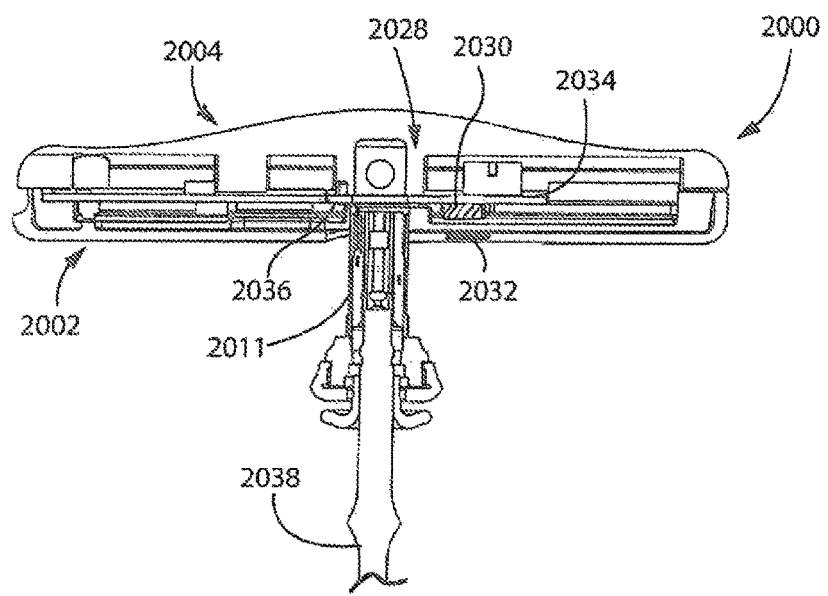
FIG. 36 is a cross-sectional view of a thirteenth embodiment of an electronic driving tool constructed according to the present invention.

Referring now to FIG. 36, the tool 2000 is shown with a lockout mechanism 2028 disposed therein. The mechanism 2028 includes a lock out switch 2030 disposed within the housing 2010 and operably connected to a circuit board 2034 located in the housing and forming the torque sensing mechanism or system 2014, which in this or any other embodiment for the wrench can be any type of conventional electronic torque sensing mechanism. When the housing 2010 is positioned within the cradle 2002, the switch 2030 is positioned over the magnet 2032 held in the cradle 2002, which activates the switch 2030 to enable the power pack/sensor module 2004 to become operable.

This embodiment in FIG. 36 also illustrates how the torque sensing mechanism 2014 includes sensors 2036 operably connected to the board 2034 and to the sleeve 2011 in order to sense the torque applied by the tool 2000 via an implement 2038 operably connected to the sleeve 2011, such as via an adapter 2052 secured to the cradle 2002 and engaged by the sleeve 2011 when inserted through the cradle 2002.

Figure 37:
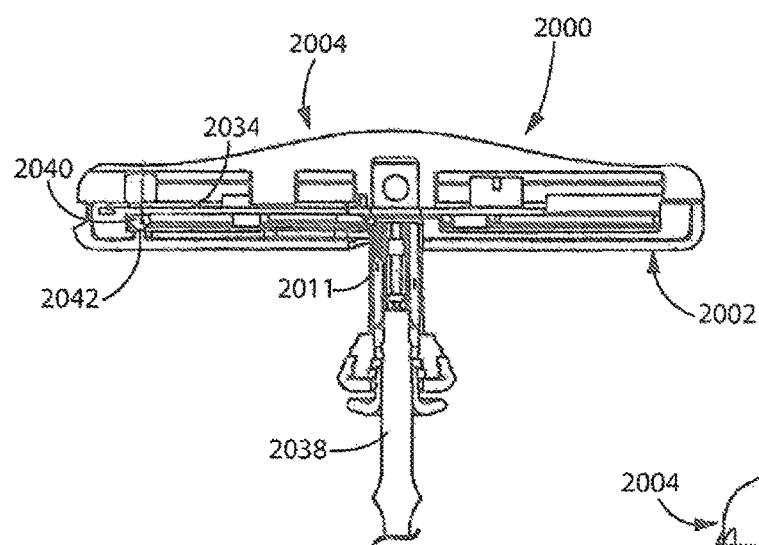
FIG. 37 is a front cross-sectional view of a fourteenth embodiment of an electronic driving tool constructed according to the present invention.

Looking now at FIG. 37, another embodiment of the tool 2000 includes a housing 2010 having an electronic lock out switch 2040 operably connected to the board 2034 that is positioned over a post 2042 on the cradle 2002 when the housing 2010 is engaged with the cradle 2002. The post 2042 contacts or otherwise operably connects with the switch 2040 to operate the switch and active the power supply of the power pack/sensor module 2004. This can be accompanied by an active power light (not shown) that is visible on the housing 2010 or on the cradle 2002 when the post 2042 engages the switch 2040.

Figure 38:
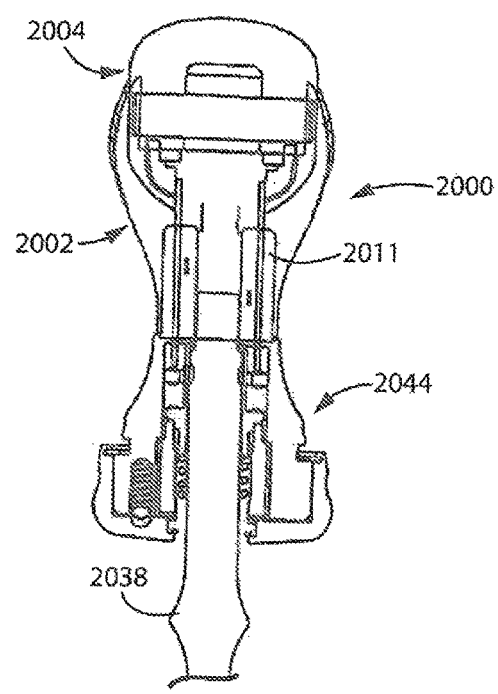
FIG. 38 is a side cross-sectional view of the tool of FIG. 37.
Figure 39:
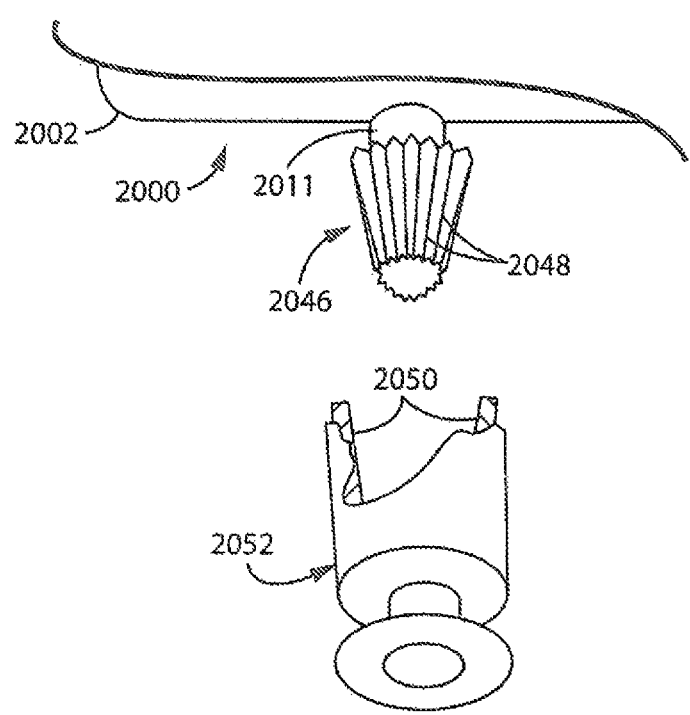
FIG. 39 is a partially broken away, isometric view of a fifteenth embodiment of an electronic driving too constructed according to the present invention.

Referring now to FIGS. 38 and 39, the tool 2000 includes a ratcheting mechanism 2044, which can be disposed within an adapter 2052 secured to the cradle 2002 and used to secure the shaft 2038 to the cradle 2002, secured to the sleeve 2011 and through which the implement shaft 2038 extends into connection with the sleeve 2011. The ratchet mechanism 2044 can be any suitable mechanism, such as that disclosed in U.S. Pat. No. 6,817,458, which is expressly incorporated by reference herein in its entirety, allows the implement 2038 to be moved in a stepwise, ratcheting manner, with each step provided with an indication of the torque exerted by the tool 2000 via the torque sensing mechanism 2014.

In a different configuration for the attachment of a ratcheting mechanism 2044 to the tool 2000, in FIG. 39 the sleeve 2011 includes a member 2046 having external splines 2048 thereon. The splines 2046 are matable with internal splines 2050 formed on a ratchet gear 2051 disposed within the adapter or connector 2052, which can be a quick release adapter. When there is a ratchet assembly or mechanism 2044 disposed in the housing for the adapter 2052, the ratchet gear is often locked in a forward or reverse position. If one is trying to assemble the power pack 2004 into the cradle 2002 that has a ratchet assembly 2044, the shaft or sleeve 2011 of the power pack 2004 has to mate with the ratchet gear 2051 to transmit torque. In order for the mating to take place the ratchet gear 2051 could be rotated until it fits/mates with the shaft 2011. However if the ratchet gear 2051 is in a locked position it cannot be rotated or in a ratchet position it can only be rotated on one direction clockwise (CW) or counter clockwise (CCW). Having a tapered splined shaft member 2046 on the mating end of the shaft 2011 allows the shaft 2011 to easily mate with the ratchet gear 2051 with internal tapered splines 2050 without rotating the ratchet gear 2051 or unlocking it. The more splines 2048 on the shaft 2011, the less the shaft 2011 needs to rotate and therefore the smoother the mating between the shaft 2011 and gear 2051, such that the power pack 2004 and the ratchet assembly 2044 can be mated without having to switch the ratchet gear position, i.e. the large number of splines 2048, 2050 allows the power pack 2004 to be assembled to the gear 2051 with minimal rotation while the gear 2051 is in a locked position.

Figure 40:
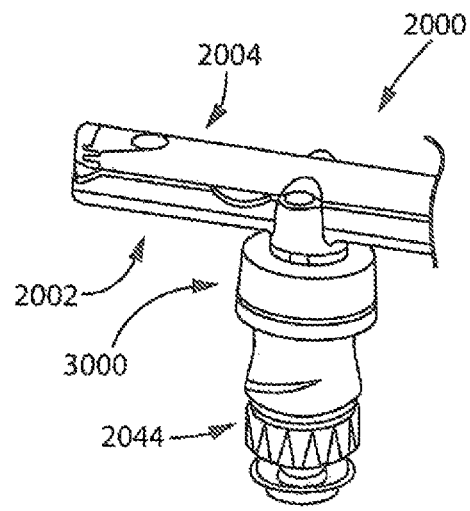
FIG. 40 is an isometric view of a sixteenth embodiment of an electronic driving too constructed according to the present invention.

In still another configuration shown in FIGS. 40-42, another embodiment, the power pack 2004 can be inserted into the cradle 2002 with the sleeve 2011 of the housing passing through the cradle 2002 for engagement with a locking collar 3000 disposed on the ratcheting mechanism 2044. The collar 3000 is rotatably mounted on the ratcheting mechanism 2044 and has an adapter 3002 therein. The adapter 3002 defines a blind bore 3004 within which the sleeve 2011 is inserted to engage the cradle 2002 and the housing 2010 with the collar 3000 and mechanism 2044. The closed end of the adapter 3002 includes a projection 3006 having a number of teeth 3008 thereon that engaged with the internal gear of the ratcheting mechanism 2044. Thus, when the sleeve 2011 is inserted within the adapter 3002, the twisting of the housing 2010 and cradle 2002, which forms the handle for the tool 2000, correspondingly moves the ratcheting mechanism 2044, and the torque applied to the mechanism 2044 any shaft 2038 attached thereto, is effectively transmitted to the module 2004 for measurement and display.

The sleeve 2011 is held within the adapter 3002 by the engagement of the collar 3000 between the mechanism 2044 and the sleeve 2011. In the illustrated embodiment, the sleeve 2011 includes a post 3010 extending outwardly from the sleeve 2011. The post 3012 is insertable within a channel 3010 formed in the collar 3000. A locking member 3014 is disposed within the collar 3000 and can be selectively engaged with the post 3012 in order to securely engage the post 3012 and the sleeve 2011 with the collar 3000. The locking member 3014 can be disengaged from the post 3012 to enable the sleeve 2011 to be withdrawn from the adapter 3002.

Looking now at FIGS. 43-45, in another embodiment for the tool 2000, the cradle 2002 is formed with the mechanism 2044 fixed to the cradle 2002 by a connecting shaft 3016. The sensor module/power pack 2004 is subsequently inserted into the cradle 2002 and connected to the connecting shaft 3016. In FIG. 44, the connection between the connecting shaft 3016 and the cradle 2002 is made by a locking pin 3018 on the shaft 3916 that is engaged within a pair of opposed notches 3020 disposed in the cradle 2002.

In this embodiment, as best shown in FIG. 45, the maximum torque that can be applied by the tool 2000 is limited by the a torque limiting mechanism 3022, such as that disclosed in U.S. Pat. No. 7,806,026, which is expressly incorporated by reference herein in its entirety. In addition, the locking pin 3018 and/or the connecting shaft 3016 can include notched sections 3024 therein. The size of these notches 3024 is selected to enable the shaft 3016 and/or pin 3018 to have a shear strength equal or approximately equal to the maximum torque to be applied by the tool 2000. Thus, when this torque level is reached, the shaft 3016 and/or pin 3018 will shear at the notch 3024, rendering the tool 2000 inoperable and incapable of applying further torque.

FIGS. 46A-46F show other alternative configurations for the housing 2010 and the corresponding insertion/engagement of the housing 2010 in the cradle 2002.

Figures 47A, 47B, 47C, 47D:
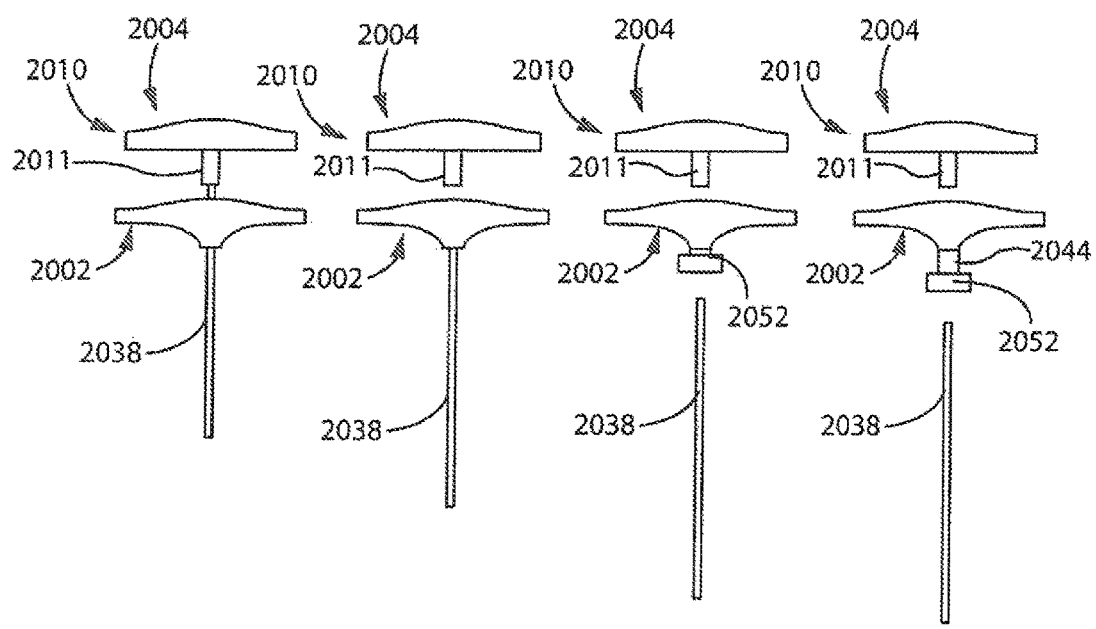
FIGS. 47A-47D are front plan views of various tools showing a power pack/sensor module with a single configuration engaged with cradles having different operating configurations.

Looking now at FIGS. 47A-47D, the tool 2000 is illustrated in which the housing 2010 and stem 2011 for the power pack/sensor module 2004 are configured in a manner that enables the same module 2004 to be used with cradles 2002 having different configurations. In FIG. 47A the housing 2010 has an implement shaft 2038 secured to the stem 2011, and the housing 2010 and shaft 2038 combination are engaged with the cradle 2002 by first inserting the shaft 2038 through the opening 2013 in the cradle 2002. In FIG. 47B, the shaft 2038 is secured to the cradle 2002, with the housing 2010 subsequently engaged with the cradle 2002 and the shaft 2038. In FIG. 47C, the cradle 2002 includes an adapter 2052 secured to the cradle 2002, and which can be used to releasably connect the shaft 2038 to the cradle 2002. In FIG. 47D, the cradle 2002 includes an adapter 2052 having a ratchet mechanism 2044 therein.

With these configurations for the tool 2000, the sensor pack 2004 is a single use item and the cradle 2002 is the reusable item as it can be sterilized. Some customers may want a device with a fixed shaft (A) in which case the cradle 2002 is very small and light and possibly the least costly. Since the cradle 2002 is in the instrument tray kit 2200, the overall instrument tray kit cost is lower.

The sensor packs 2004 used in options B, C and D are identical to each other and the only difference to option A is that the entire length of the shaft 2038 is attached to the sensor pack 2004.

Having identical configurations for the sensor pack 2004 allows the end user to buy and stock one sensor pack 2004 and still use it on any of the three different cradle options 2002. From the manufacturers view point having an almost identical sensor pack 2004 construction across options A-D allows for higher volumes and hence lower items costs.

B: this option allows the end user to buy a lower cost sensor pack 2004 which is a single use item since a sensor pack 2004 with a shorter shaft is less costly to manufacture and ship.

C: this options allow the end user to use any shaft 2038 that has appropriate mating features with the tool 2000 (sensor pack 2004+cradle 2002). End user may use multiple shafts 2038 custom to each implant or across various implants.

D: this option allows the end user to use any shaft 2038 and have the ability to ratchet the device to appropriately position the tool 2000 for ease of use.

Figure 48:
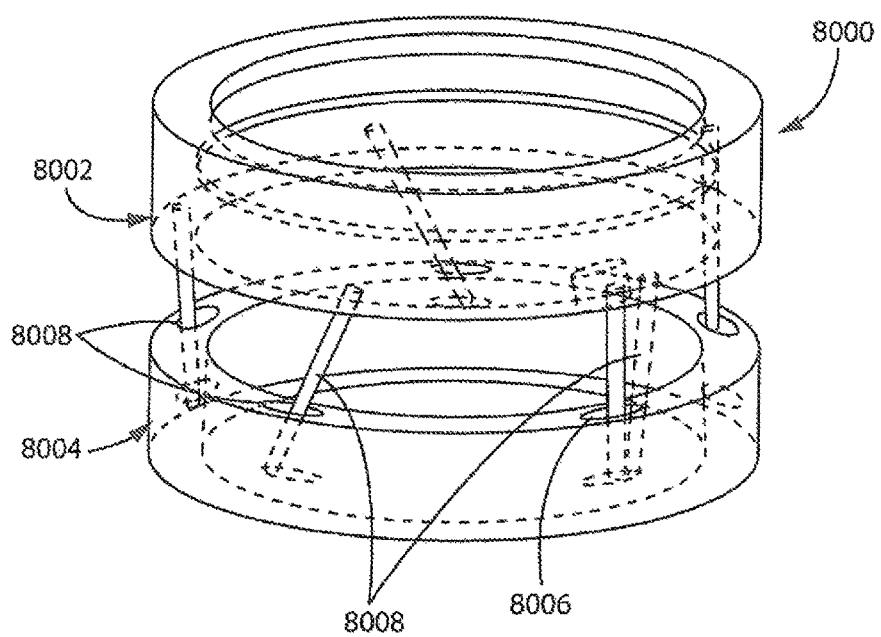
FIG. 48 is an isometric view of a locking and fixed collar arrangement of the tool of FIG. 47A-47D.

Further, in FIG. 48, one configuration for a connector 8000 for securing the pack 2004 to the cradle 2002 and shaft 2038 that utilizes a locking ring 8002 and a fixed ring 8004, each having bores 8006 therein within which are placed opposed ends of spring pins 8008 to control the movement of the rings 8002 and 8004 with respect to one another.

Figure 49:
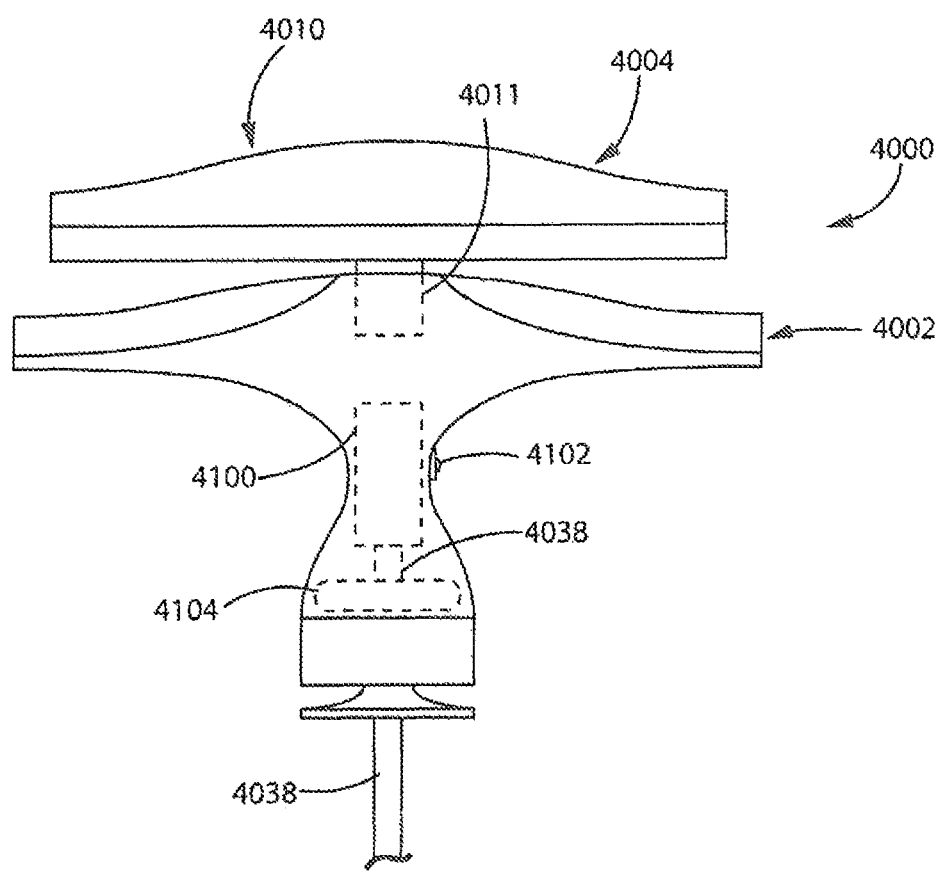
FIG. 49 is an isometric view of an eighteenth embodiment of an electronic driving too constructed according to the present invention.

In another embodiment of the tool 4000 shown in FIG. 49, in order to provide an alternative safety aspect to the tool 4000, the cradle 4002 includes a mechanical torque-limiting mechanism 4100 disposed within the cradle 4002 and engaged at one end with the shaft 4038 and at the other end with the stem 4011 on the housing 4010 of the sensor pack 4004 to operably connect the torque sensing device 4014 in the sensor pack 4004 with the shaft 4038 to measure the torque applied by the tool 4000. The torque-limiting mechanism 4100 can be any suitable mechanism, such as that disclosed in U.S. Pat. No. 7,650,821, which is expressly incorporated by reference herein in its entirety. In the event that the sensor pack 4004 malfunctions and does not provide accurate indications to the used of the torque being applied by the user through the tool 4000, the torque-limiting mechanism 4100 will operate in a mechanical manner to prevent excessive torque from being applied by the tool 4000.

In addition, in conjunction with the mechanism 4100, the tool 4000 can include an indicator 4102 operably connected to the mechanism 4100 that provides an indication to the user of the tool 4000 that the mechanism 4100 has exceeded its torque limit. One example of such a mechanism 4102 is disclosed in U.S. Pat. No. 7,806,026, previously incorporated by reference herein in its entirety.

Further, the tool 4000 can include a variable gear ratio drive mechanism 4104, such as that disclosed in U.S. Patent Application Publication No. US2010/0294084, which is expressly incorporated by reference herein in its entirety.

Figure 51:
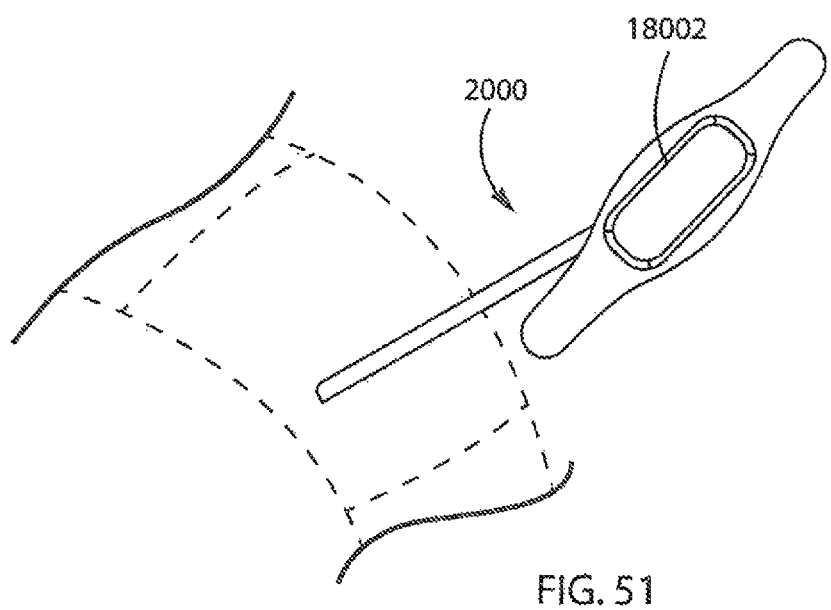
FIG. 51 is a schematic view of a twentieth embodiment of an electronic driving tool constructed according to the present invention.
Figure 50:
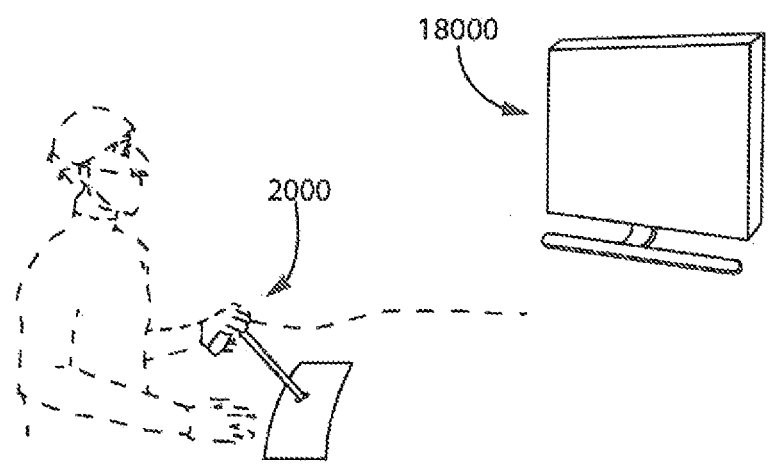
FIG. 50 is a schematic view of a nineteenth embodiment of an electronic driving tool constructed according to the present invention.

In FIGS. 50 and 51, embodiments of the tool 2000 are shown in which the sensor module 2004 is operably connected to a video screen 18000 that an display the torque values sensed by the module 2004, or that includes a display 18002 on the module 2004 capable of displaying the sensed torque values, and also functioning as a video screen to display the site on which the individual is using the tool 2000. In the illustrated embodiments, FIG. 50 shows a tool 2000 connected wirelessly to the display 18000, while FIG. 51 shows a display 18002 disposed directly in the tool 2000.

Figure 52:
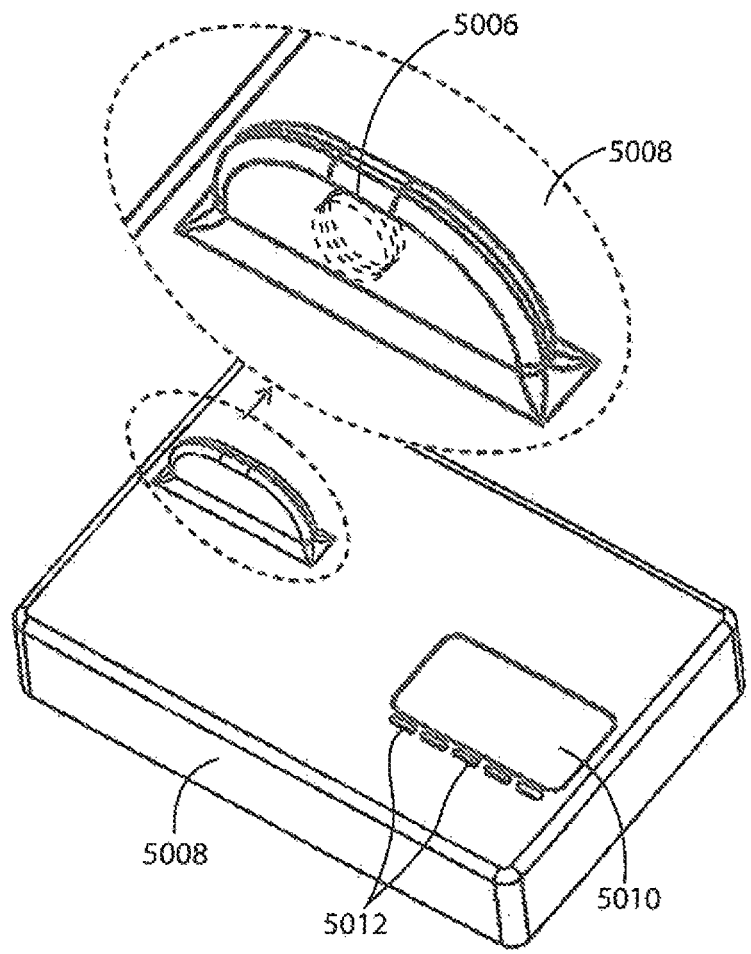
FIG. 52 is a an isometric view of a charging station for a driving tool constructed according to the present invention.
Figure 53:
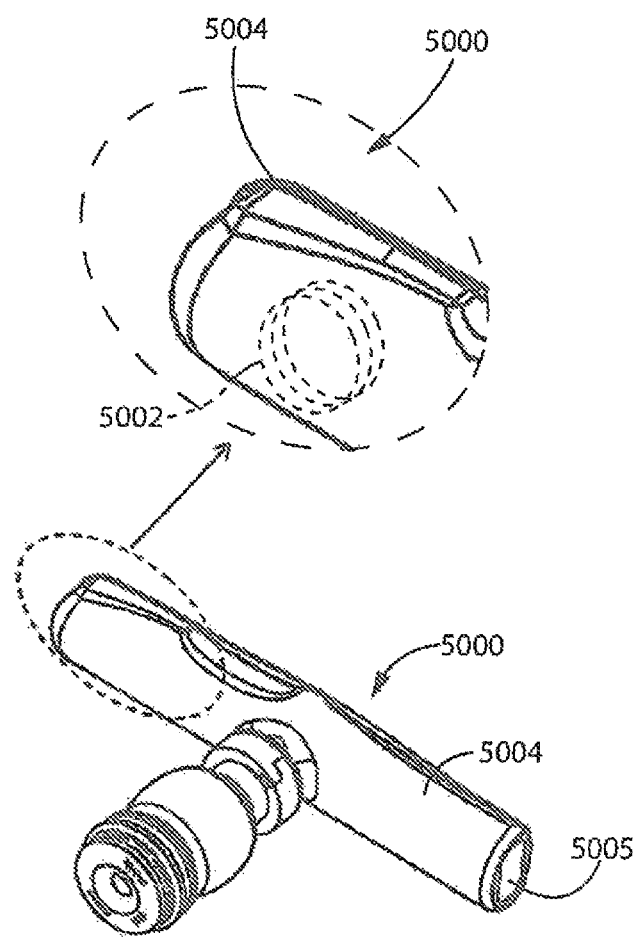
FIG. 53 is an isometric view of a twenty-first embodiment of a driving tool constructed for use with the charging station of FIG. 52.
Figure 54:
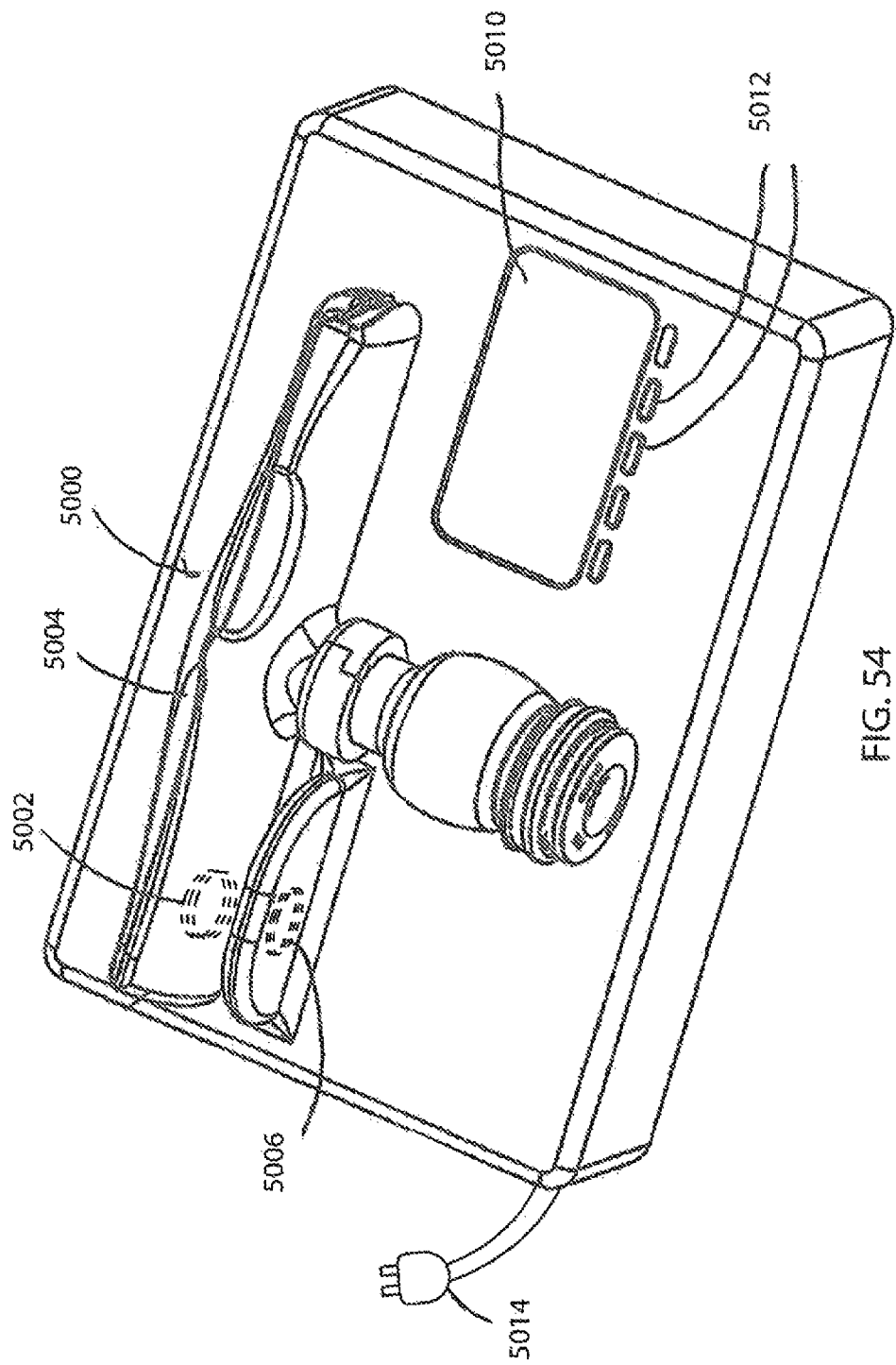
FIG. 54 is an isometric view of the driving tool of FIG. 53 charging on the charging station of FIG. 52.

Looking now at FIGS. 52-54, a twenty first embodiment of the tool 5000 is illustrated in which the tool 5000 includes, among other features shown in prior embodiments such as an adapter 5028 and a ratcheting mechanism 5044, among others, a receiver coil 5002 disposed within a portion of the handle 5004 for the tool 5000 and operably connected to the other electronic components in the tool 5000, such as a battery pack 5005 and torque measuring mechanism (not shown) and display (not shown). The receiver coil 5002 is able to be positioned in electrical contact with a transmitter coil 5006 disposed on a charging station 5008 in order to provide a wireless, inductive charge through the receiver coil 5002 to the battery pack. The station 5008 includes features to properly align and maintain the alignment of the tool 5000 and receiver coil 5002 with the transmitter coil 5006 on the station 5008, to ensure a proper charge when the tool 5000 is positioned on the station 5008. Additionally, the station 5008 includes a power cord 5014 that enables the station 5008 to be supplied with power via any conventional power outlet, such as a wall outlet (not shown). The station 5008 can also include a display 5010 that provides various information on the status of the station 5008 and of the tool 5000 placed on the station, including, but not limited to the status of the charging of the tool 5000 on the station 5008, which can be altered by using selector buttons 5012 on the station 5008. Some advantages of this construction for the tool 5000 include:

1. Wireless battery charging allows a rechargeable battery to be sealed in the device 5000. This way the battery is sterilized within the device 5000. This eliminates the need to handle a battery pack and load the battery pack into the device while using aseptic techniques. Therefore improved safety for the patient. Since the charging is wireless both the charger 5008 and the device 5000 do not need exposed metal contacts and thus can be sealed which makes them safer to use and clean/sterilize for use in an operating room environment which often involves exposure to moisture especially during the cleaning process, such as steam cleaning/autoclaving.
2. Principle of operation: Power is transmitted by inductive coupling. The system involves two devices, the battery powered device 5000 and the wireless charger 5008. The charger 5008 has a transmitting coil 5006 which transmits power to the receiver coil 5002 which is located in the device 5000 when the receiver coil 5002 is placed in the magnetic field created by the transmitting coil 5006 by inductive coupling. The receiver coil 5002 is connected to a rechargeable battery. This battery supplies power to the circuit within the handle 5004. The transmitter and receiver coils transmit power using high frequencies (radio frequencies) this power charges up the battery. The two coils are tuned to each other to make this energy transfer possible. The closer together these coils are placed and the better they are aligned the more efficient the power transfer will be. Image shows the device placed near the coil in the charger. A custom fitted stand could be designed for best alignment or a more generic mat type charger could be used to charge multiple devices at once. Related patents for wireless power transmission include U.S. Pat. Nos. 3,938,018; 5,314,453; 5,314,457 and 8,378,523, each of which are expressly incorporated by reference herein in their entireties.

Figure 56:
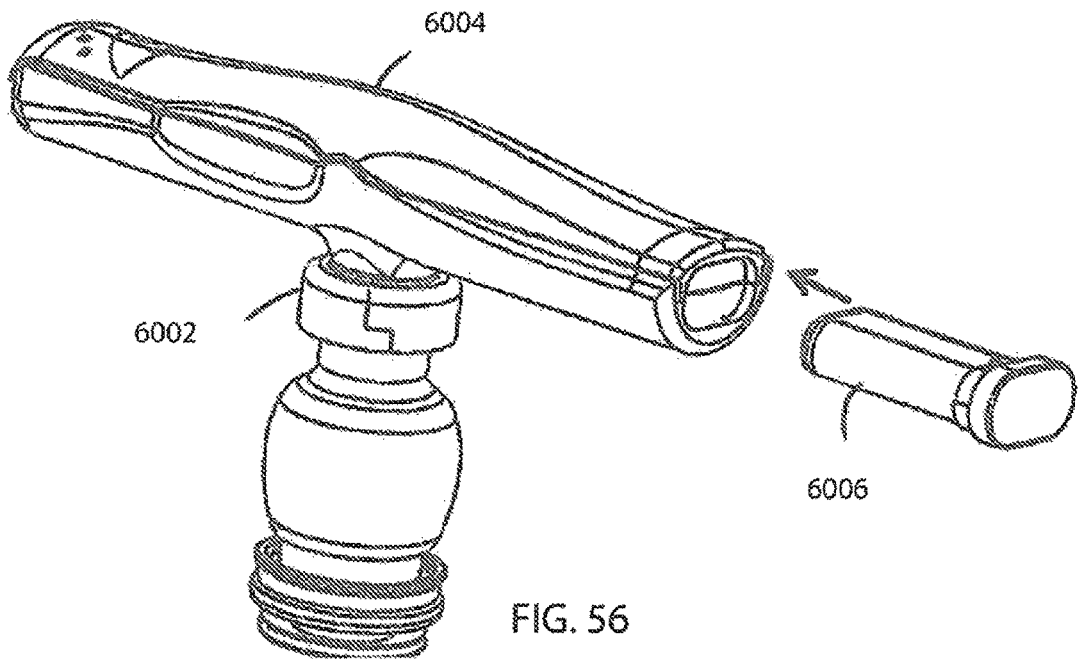
FIG. 56 is a partially exploded view of the tool of FIG. 55.
Figure 55:
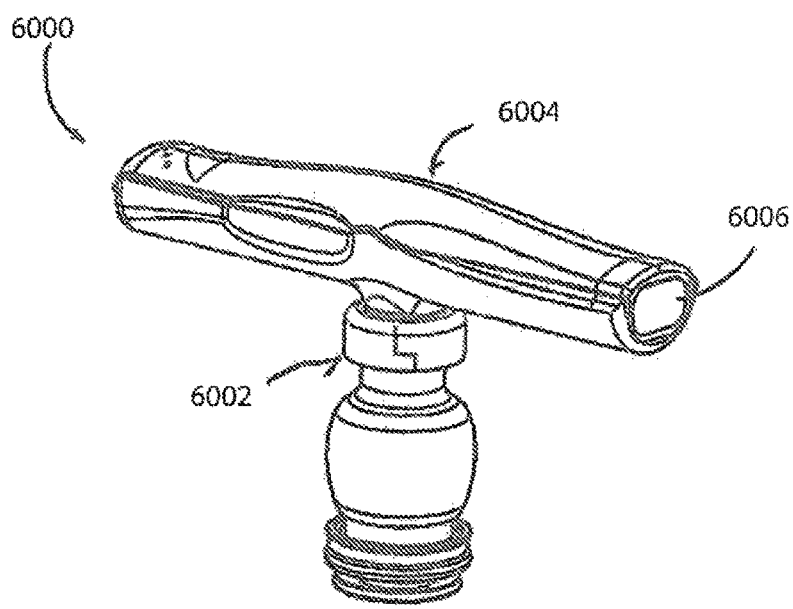
FIG. 55 is an isometric view of a twenty-second embodiment of a driving tool constructed according to the present invention.
Figure 57:
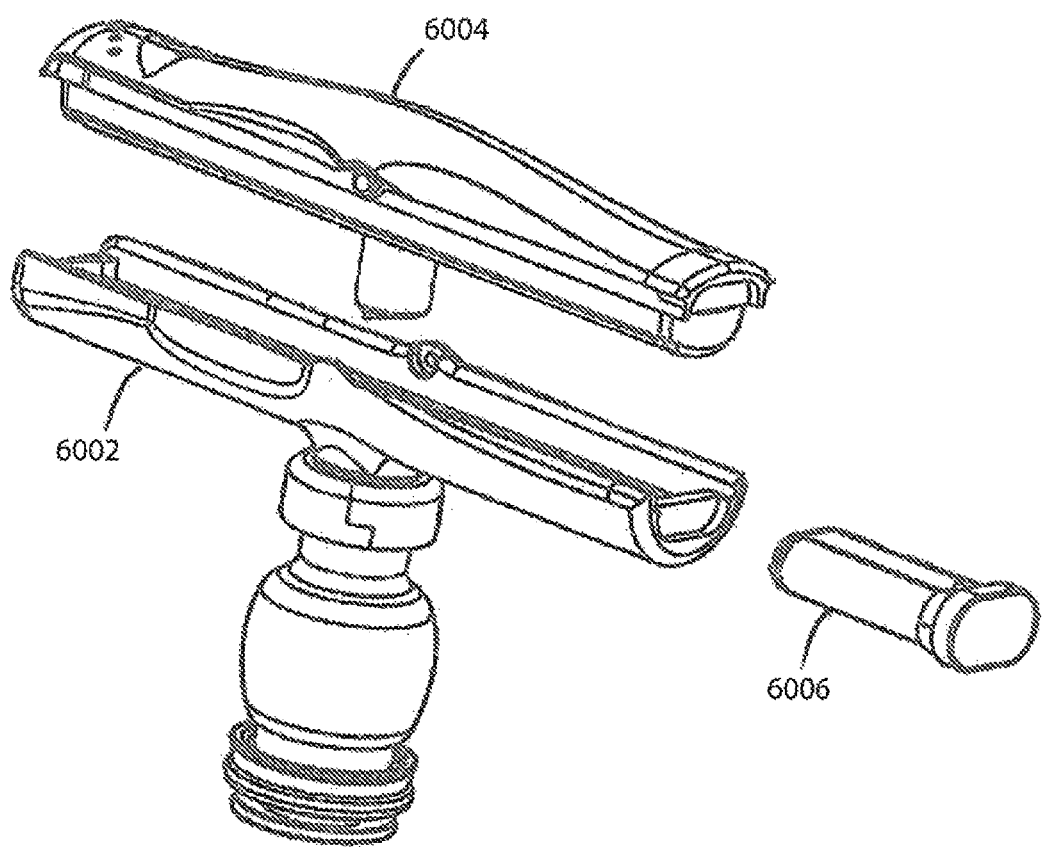
FIG. 57 is a fully exploded view of the tool of FIG. 55.

Referring now to FIGS. 55-57, in order to enable the use of prior art rechargeable non-sterile batteries in sterile surgical instruments or tools 10, 2000, 6000, as described in U.S. Pat. No. 6,917,183, which is expressly incorporated by reference herein in its entirety, users employ a known "sterile transfer" technique. While possibly known by other names, this technique generally entails the sterilization and use of a sterile battery container to be attached to a sterile powered instrument. The sterilized container is held in a sterile field (by a scrub nurse, for example) and is shielded by a sterile shroud. A non-sterile, charged battery (held by a circulating nurse, for example) is placed into the sterilized container with care so as not to contaminate the already sterilized container. The shroud is then removed by the circulating nurse and the sterilized container is closed by the scrub nurse and attached to the instrument. The container hermetically encloses the battery and has its own exterior terminals which are connected to the battery terminals and through which the instrument is powered.

The battery used is generally a battery pack comprising a plurality of individual battery cells wired and bound together in one unit. The terminals of the cells are connected in series and to the terminals of the battery pack. As used herein, the term "battery" will be understood to include a battery pack.

Prior art battery packs generally have terminal contacts which are surface mounted and engageable by contiguous engagement with another surface contact in the device with which the battery pack is designed to operate. The surface contacts are designed to be pressed toward each other, essentially pushing in opposite directions along an imaginary line passing through both contacts at the point at which they are contiguous. Sometimes a spring force is designed into the engagement to enhance the force with which the terminal contacts press against the device contacts.

Surface contacts are subject to vibration in powered surgical instruments and this may increase wear and affect performance. Also, surface contacts may subject a battery to risk of shorting if the battery terminals inadvertently connect conductive materials before being put into the intended instrument.

Additionally, surface contacts necessarily increase the size of the battery and/or battery/instrument combination. This occurs simply because of the necessity of providing relatively massive contacts and/or spring mechanisms to maintain a secure connection during use. Further, the battery packs that are sealed to be steam sterilized to address these concerns would necessarily lose a lot a significant portion of the stored charge when heated up to sterilization temperatures which are as high as 134° C. (273.2° F.).

To address these concerns and shortcomings of prior art rechargeable battery packs that cannot survive the harsh environment of steam sterilization in an autoclave, and since steam sterilization is the most commonly used method for sterilizing instruments, a twenty-second embodiment of the tool 6000 shown in FIGS. 55-57 and 60-64 is constructed with three sub-assemblies, namely, a handle base or cradle 6002, which can include attributes of the prior embodiments, such as an adapter, a ratcheting mechanism, torque-limiting mechanism, lighting assembly, etc., a sensor pack 6004 engageable with the handle 6002, and a replaceable and rechargeable battery pack 6006 engaged with the handle 6002 and sensor pack 6004. Each sub-assembly has a different "life expectancy" in the harsh environment of steam sterilization. In one embodiment:

1. Part 1—HANDLE BASE 6002 with quick connect collet/adapter 6028 and ratcheting mechanism 6044; this is reusable and steam sterilizable up to at least 150 autoclaves.
2. Part 2—SENSOR PACK 6004 (contains electronics making up electronic torque sensing mechanism 6014, electronics unit 6020 and display 6022, and can be fixed or releasably connected to the base 6002)—reusable up to approx. 100 autoclaves
3. Part 3—BATTERY PACK 6006 can also, in certain embodiments, contains the buzzer and vibrating motor (not shown) in addition to the battery pack and connector—is designed for a single use. Battery pack 6006 is sterilized by EtO and is sold sterile in a sealed pouch and is not intended for steam sterilization. Each component has benefits making the surgical procedure safer, simpler and reducing patient risk and improving outcomes. The main area of risk is in the cleaning and sterilization. By using a sealed and EtO sterilized battery pack the user is sure to receive a fully charged battery pack. If the procedure lasts too long they can open a fresh battery pack.

4. Part 4—STERILE INSERTION SHIELD 6040 can also optionally be utilized with non-sterilized battery packs 6006' in a second embodiment shown in FIGS. 60-64.

The single use battery pack 6006 has many advantages over a rechargeable battery, including:

1. If the device 6000 is dropped on the floor during a surgery the surgeon can dispose of the non-sterile battery pack 6006, the surgical staff can clean and flash sterilize the device 6000 within minutes and load a new sterile battery pack 6006 thereby avoiding the wait for a battery to be recharged. Another benefit is that no battery charger is required.
2. The battery pack 6006 is sterilized and sold sterile in a sealed pouch so the risk of infection from an improperly cleaned rechargeable battery is reduced.
3. In an alternative embodiment where the single use battery pack 6006' is not sterilized prior to use, best shown in FIGS. 60-64, the battery pack 6006' is designed not to be steam sterilizable, resulting in a smaller volume and lighter battery pack 6006' than required for steam sterilizeable battery packs 6006, since steam sterilizeable battery packs 6006 typically have the additional mass of heat shielding materials to encapsulate the batteries and more than necessary chemical mass to compensate for the amount of charge lost due to the high temperatures of steam sterilization (250-275° F.). Additionally, non-sterile battery packs 6006' last much longer than sterilizeable battery packs 6006 because they do not repeatedly undergo the extreme conditions of steam sterilization, and do not have the battery and/or other electronics disposed within the battery pack 6006' potentially damaged by the sterilization process. Further, non-sterilizeable battery packs 6006' can be safer to use since they are not exposed to high heat and therefore less chance of explosion.

The device 6000 in this embodiment also has electronics (not shown) therein, e.g., in the handle 6002, the sensor pack 6004 or the battery pack 6006, that will count the number of times the device 6000 was powered on, alone or in conjunction with other electronics within the device 6000, and can notify the user of device life left and when to replace the sensor pack 6004.

In another embodiment, the device 6000 can have electronics (not shown) therein, e.g., in the handle 6002, the sensor pack 6004 or the battery pack 6006, that will count the number of times the device 6000 was autoclaved, alone or in conjunction with other electronics within the device 6000, and can notify the user of device life left and when to replace the sensor pack 6004.

Figure 62:
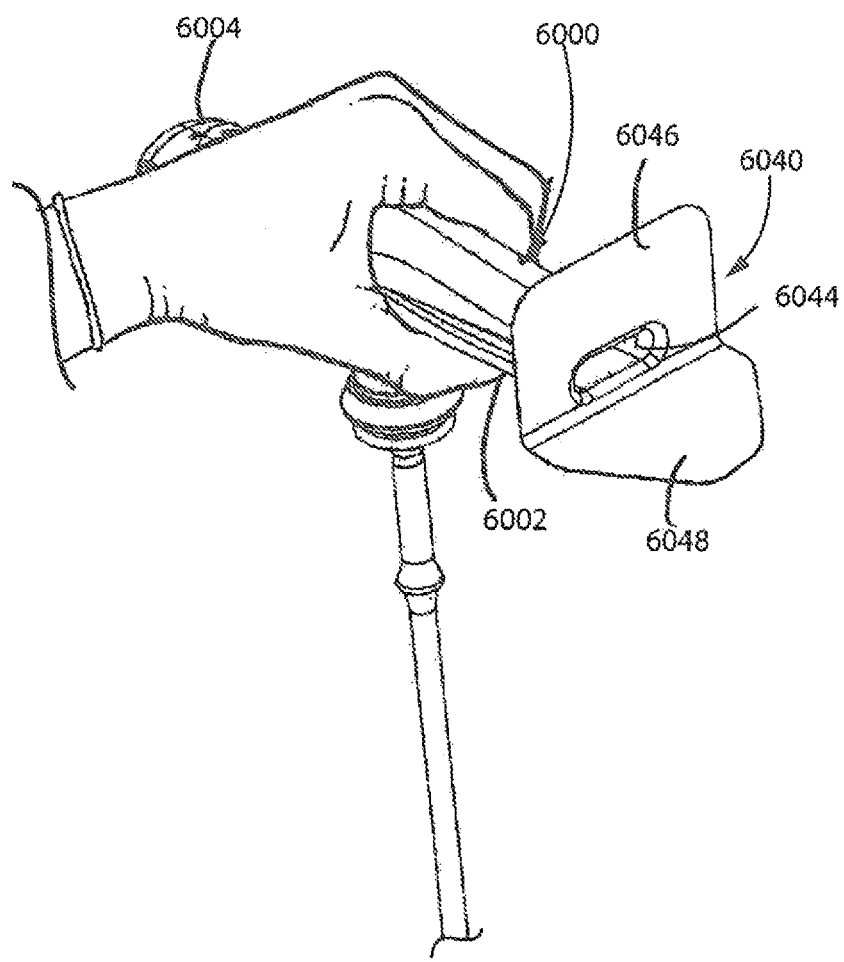
FIG. 62 is an isometric view of the shield of FIG. 61 engaged with the tool of FIG. 60.
Figure 63:
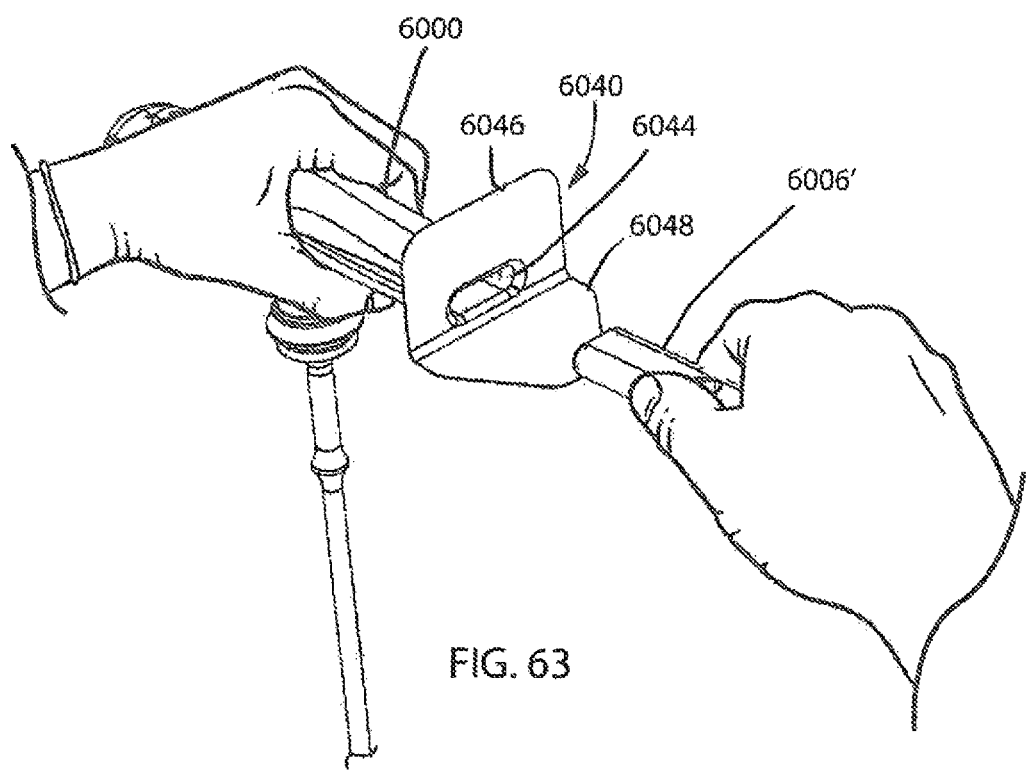
FIG. 63 is an isometric view of the insertion of the non-sterile battery pack into the tool of FIG. 60 through the shield of FIG. 61.
Figure 64:
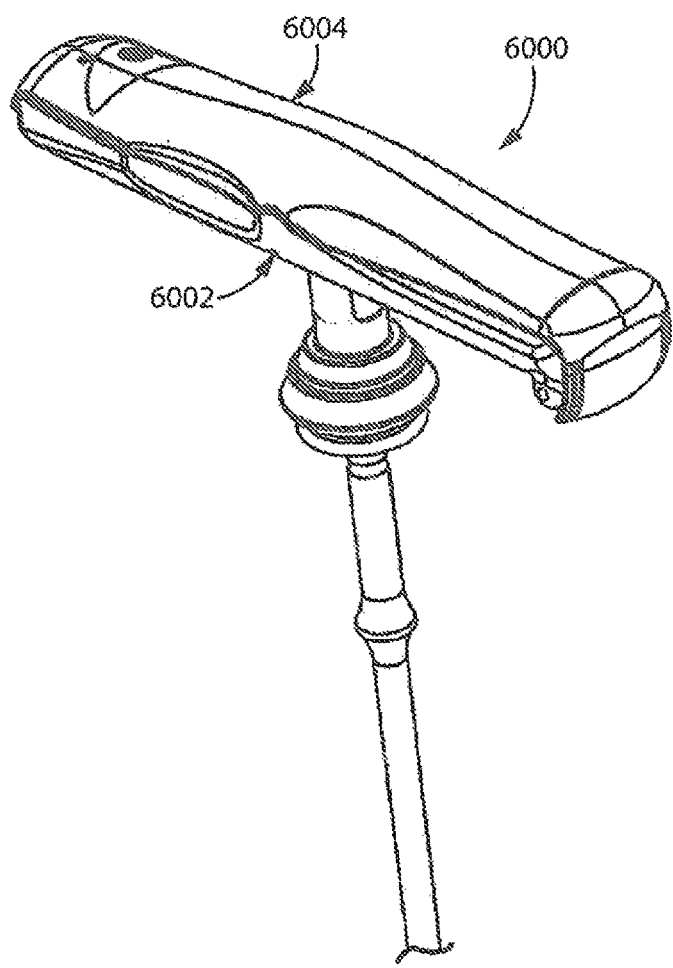
FIG. 64 is an isometric view of the driving tool of FIG. 60 in a closed position with the non-sterile battery pack retained therein.

When a non-sterilizable battery pack 6006' is utilized, the aseptic transfer process for using this type of battery pack 6006' is shown in FIGS. 60-64. Initially, in FIG. 60, the sterile handle 6002 or sensor pack 6004 of the device 6000 is opened by an individual I in the sterile field to expose the chamber 6042 in which the battery pack 6006' is to be positioned. In the open position, the chamber 6042 can be engaged by the individual I in the sterile field with a sterile shield 6040 (FIG. 61) that includes a sleeve 6044 that is releasably engageable within the chamber 6040 and a number of shielding surfaces 6046,6048 surrounding and/or extending outwardly from the sleeve 6044. The surfaces 6046,6048 allow access to the chamber 6042 through the sleeve 6044 while preventing direct contact with the chamber 6042 or any other surface of the device 6000. In FIG. 62 the shield 6040 is illustrated with the sleeve 6044 partially engaged within the chamber 6042 to enable the chamber 6042 to be exposed while also protecting the remaining surfaces of the handle 6002, sensor pack 6004 and device 6000 using the surfaces 6046,6048. In FIG. 63, an individual O outside of the sterile filed then inserts a non-sterile battery pack 6006' into the chamber 6042 through the sleeve 6044 of the shield 6040, while preventing the non-sterile individual from contacting the sterile device 6000. Once the non-sterile battery pack 6006' is fully inserted within the chamber 6042, the sleeve 6044 of the shield 6040 can be removed from around the battery pack 6006' by the individual outside the sterile field, and the individual in the sterile field can close the handle 6002 without contacting the battery pack 6006' and activate the device 6000 including the non-sterile battery pack 6006'.

Figure 58:
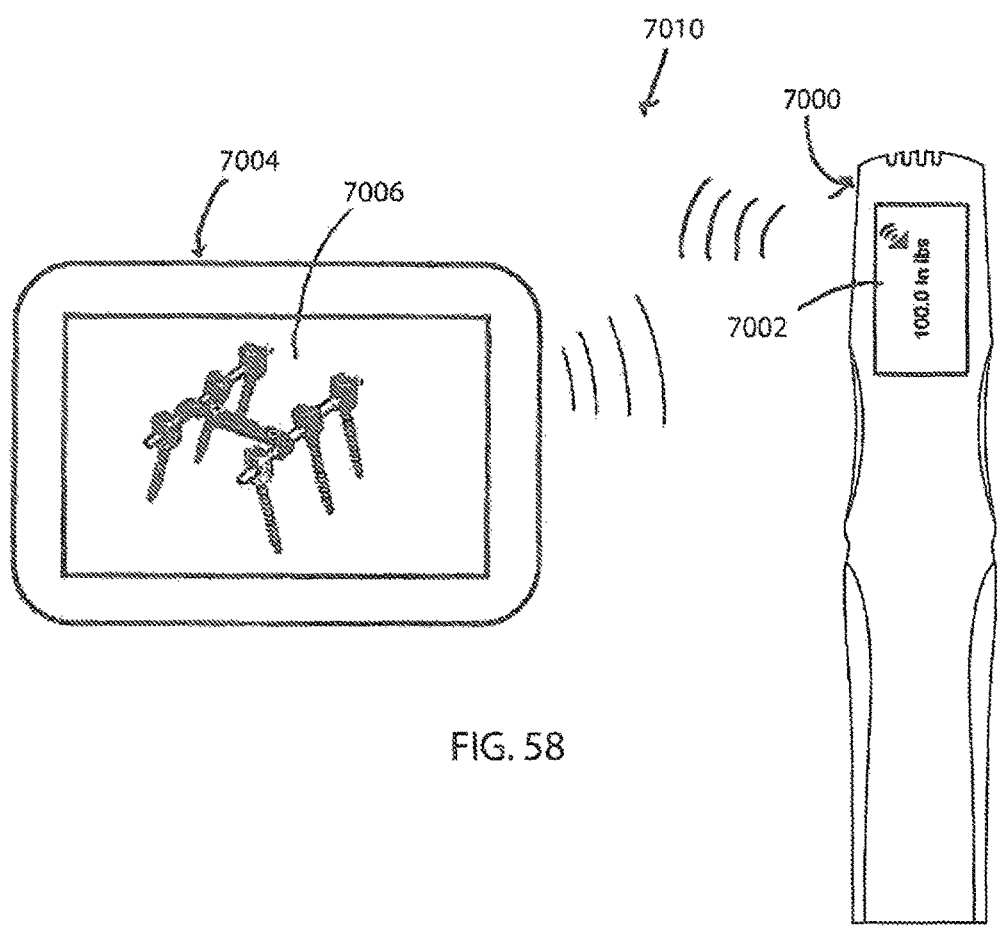
FIG. 58 is a schematic view of a twenty-third embodiment of a driving tool constructed according to the present invention; a FIGS. 59A-59E are schematic views of a display of the tool of FIG. 58.
Figure 61:
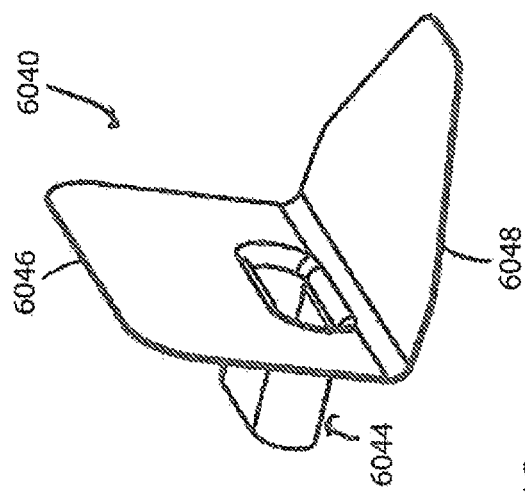
FIG. 61 is an isometric view of a sterile shield for use with the tool of FIG. 60.
Figure 60:
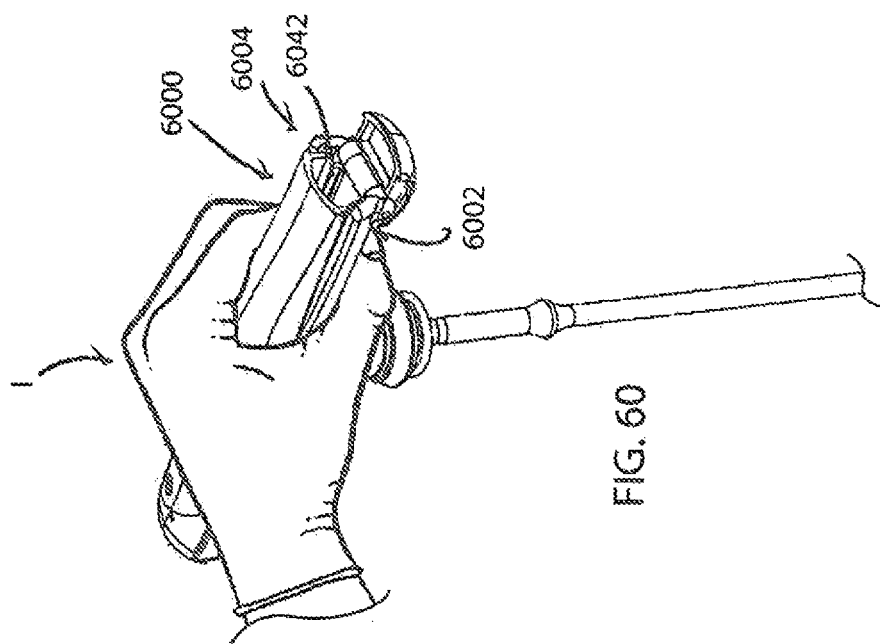
FIG. 60 is an isometric view of an embodiment of the driving tool of FIG. 55 in an open position for use with a non-sterile battery pack.

Looking now at FIGS. 58-59E, in a twenty-third embodiment of the device 7000, the device 7000 can include any features of any prior embodiment, and as illustrated includes a display 7002 and includes a suitable transceiver (not shown) configured to transmit and/or receive information using a suitable protocol (NFC, RFID, Bluetooth, etc.) from a separate electronic computing device 7004, such as a desktop computer, laptop computer, or tablet computing device, among others that can also include a display 7006. The communication between the device 7000 and the computing device 7004 enables the torques being applied by the device 7000 to be transmitted and stored in the device 7004, or in a suitable electronic data storage medium or location operably connected to the device 7004.

In one embodiment, the recording feature for the electronic torque wrench 7000 can transmit data wirelessly to an app on the device 7004. The app ("App" is an abbreviation for application; "App" definition: An app is a piece of software. It can run on the internet, on a computer, on a phone or other electronic device.) can run on a device 7004 with any suitable operating system, such as an android or iOS device. The procedure would involve the initial step where the doctor opens the app on the device 7004 which would show the image of the entire construct being implanted in the procedure. The electronic torque wrench 7000 would subsequently be set to transmit mode. The surgeon could even take this image of the construct during surgery. Now the surgeon would touch the screen image of the fastener on the display 7006 of the device 7004 he/she is about to tighten, the app would then present the appropriate torque values for the tightening the fastener, upload the values to the device 7000 for use by the surgeon tightening the particular fastener. Now the surgeon would proceed with using the ETW 7000 to tighten the fastener on the construct, and the device 7004 would record the torque values that are being transmitted by the device 7000 to be saved on the device 7004 or similar smart electronic device with a link that appears in the pixel grid location that the surgeon tapped. The surgeon then touches the next fastener he/she is about to tighten then tightens and fastener and so on, and in one embodiment performs this function using a predetermined sequence for tightening the fasteners provided by the information displayed on the device 7004.

Data retrieval: When retrieving the data from the device 7004, the person retrieving the data would be able to play each torque data file by touch the links provided in the each pixel location on the screen image.

In this embodiment, NFC (Near Field Communication) or RFID (Radio-frequency identification) can be used to establish a connection between the ETW 7000 and the electronic device 7004, like a mobile phone or ipad. For higher data transfer rates, a wireless connection like Bluetooth can be used which is capable of higher data transmission rates. The ETW device 7000 could be coupled to other electronics devices (not shown) like monitors to display live streaming torque data or replay recorded data.

As shown in FIGS. 59A-59E, the ETW 7000 could have a screen 7002 with buttons or no screen and buttons. In the case of no buttons and screen the ETW 7000 could be controlled and even activated by the presence of the compatible RFID, NFC or Bluetooth capable or similar devices. This data includes downloading data recorded on the ETW 7000 or playing a video of the data being recorded on the NFC app.

Since NFC is a very simple way to establish a link between two devices this could be used to establish the link while Bluetooth connections can be used to transfer data between the two devices. Examples of this are Nokia and Sony that use NFC to pair Bluetooth headsets and speakers with a tap in a NFC device.

Patient data security is inherent in the type of communication being 'near field' which is currently 4 to 10 cm. Another way to add security is for security codes to also be programmed into the NFC tags (un powered NFC chip is called a tag) on the two communicating devices. This could be monitored by a microcontroller which looks for and checks the security codes on both devices before allowing the communication to proceed between them.

RFID tags used with the device 7000 can be either active or passive. RFID communication between two devices can be of the following types.

Passive Reader Active Tag (PRAT)
Active Reader Passive Tag (ARPT)
Active Reader Active Tag (ARAT)

With regard to the utility of the tool/device 7000, the following are some reasons for the usefulness of this embodiment of the device 7000, and some descriptions of alternative embodiments of a system 7010 employing the devices 7000 and 7004.

It assures the surgeon that the correct torque was applied.
In an investigation a record of correctly torqued fasteners would help vindicate the surgeon, hospital and the implant OEM.
In a case where there are complications a more precise torque instrument will mean there is one less chance of error that the surgeons need to be concerned with.
More accuracy may also be important in cases that may start out simple but become complicated.
A more precise torque wrench on the market could lead to OEMs designing new implants that need this higher precision.
This higher precision could be desired on surgeries like cochlear implantations that require very low precise torques. Additionally not having a sharp jarring from a torque limiting mechanism may be desirable in delicate surgeries.
A wireless display would allow the surgeon to see the torque value on the video screens along with real time surgical video and other vital patient information. They would not have to move their eyes from the video screen to the torque handle. The surgeon would only look at an indicator wrench, they would not look at a torque limiting wrench. The surgeon would not use a torque if they were using a break-away driver with a type of screw in which the head breaks off when the appropriate torque is met or exceeded.

The device 7000 can also include a recording/memory storage function that allows the surgeon to record the values of the torque applied to each fastener. The benefit of this feature is that the surgeon would have proof of the torque applied to each fastener in case a fastener, a rod or some other part of the construct became loose and there was a question of whether the correct torque was applied during the procedure.

Concept #1 for the recording feature: the surgeon would use a suitable portable computing device, such as a tablet computer or similar touch screen device 7004 with the image of each fastener superimposed over the image of the anatomy, then the surgeon could touch the fastener on the tablet device 7004
then push the record button on the torque meter for the device 7000 and then tighten the fastener.

The device 7000 would then record the peak torque value and transmit the value to the device 7004 where the software would tie the image of the fastener to the torque value recorded.

Concept#2 for the recording feature: the device 7000 would have navigation orbs (not shown) attached to it which would communicate its location to the navigation software on the device 7000 or 7004.

When a record button (not shown) on the device 7000 is activated, the device 7000 records the torque value and the location coordinates of the applied torque. The navigation software then keeps this torque record along with images of the construct which ties the fastener location to the torque value recorded.

While the concepts of the present disclosure will be illustrated and described in detail in the drawings and description, such an illustration and description is to be considered as exemplary and not restrictive in character, it being understood that only the illustrative embodiments are shown and described and that all changes and modifications that come within the spirit of the disclosure are desired to be protected. There are a plurality of advantages that may be inferred from the present disclosure arising from the various features of the apparatus, systems, and methods described herein. It will be noted that alternative embodiments of each of the apparatus, systems, and methods of the present disclosure may not include all of the features described yet still benefit from at least some of the inferred advantages of such features disclosed in other embodiments which are deemed to be included in the disclosures of each of the various embodiments disclosed herein. Those of ordinary skill in the art may readily devise their own implementations of an apparatus, system, and method that incorporate one or more of the features of the present disclosure and fall within the spirit and scope of the disclosure as defined by the appended claims.

The invention claimed is:

1. A driving tool comprising:
a) a shaft engageable with a fastener;
b) a housing capable of being subjected to temperatures and pressures associated with medical sterilization procedures and including an electronics unit including a torque measurement system operably connected to the shaft and operable to measure the torque exerted though the shaft on a fastener; and c) a body defining a sleeve therein, wherein the housing is positioned at least partially within the sleeve.

2. The tool of claim 1 wherein the housing is removably positioned within the sleeve.

3. The tool of claim 1 further comprising a power source operably connected to the electronics unit.

4. The tool of claim 3 wherein the power source is positioned within the housing.

5. The tool of claim 4 wherein the power source is positioned within the body.

6. The tool of claim 3 wherein the housing is not fully inserted into the sleeve.

7. The tool of claim 6 wherein the housing includes lighted indicators disposed within the housing at a location outside of the sleeve.

8. The tool of claim 6 wherein the housing includes lighted indicators disposed within the housing alignable with a window in the body.

9. The tool of claim 1 wherein the housing is affixed to the shaft.

10. The tool of claim 1 wherein the body is affixed to the shaft.

11. A method of driving a fastener into a substrate comprising the steps of:
   a) providing the tool of claim 1; and
   b) engaging a fastener with the tool.

* * * * *